US005955646A

United States Patent [19]
Gelvin et al.

[11] Patent Number: 5,955,646
[45] Date of Patent: Sep. 21, 1999

[54] CHIMERIC REGULATORY REGIONS AND GENE CASSETTES FOR EXPRESSION OF GENES IN PLANTS

[75] Inventors: Stanton B. Gelvin, West Lafayette, Ind.; Randal Hauptmann, Davis; Min Ni, Albany, both of Calif.; Decai Cui, Chandong, China

[73] Assignees: Biotechnology Research And Development Corporation, Peoria, Ill.; Purdue Research Foundation, West Lafayette, Ind.

[21] Appl. No.: 08/619,524

[22] PCT Filed: Nov. 17, 1997

[86] PCT No.: PCT/US94/12946

§ 371 Date: Jul. 31, 1996

§ 102(e) Date: Jul. 31, 1996

[87] PCT Pub. No.: WO95/14098

PCT Pub. Date: May 26, 1995

Related U.S. Application Data

[63] Continuation-in-part of application No. 08/155,067, Nov. 19, 1993, abandoned.

[51] Int. Cl.$^6$ .............................. C07H 21/04; C12N 5/14; C12N 15/82
[52] U.S. Cl. .................. 800/205; 435/172.3; 435/320.1; 435/419; 536/24.1
[58] Field of Search ................................ 536/23.1, 24.1; 435/172.3, 320.1, 419; 800/200

[56] References Cited

U.S. PATENT DOCUMENTS

| | | | |
|---|---|---|---|
| 4,771,002 | 9/1988 | Gelvin ................................... | 435/172.3 |
| 5,106,739 | 4/1992 | Comai et al. ......................... | 435/172.3 |
| 5,164,316 | 11/1992 | McPherson et al. ................. | 435/240.4 |
| 5,196,329 | 3/1993 | Gurley et al. ......................... | 435/172.3 |
| 5,281,530 | 1/1994 | Sick et al. ............................. | 435/252.3 |
| 5,322,932 | 6/1994 | Narva et al. ............................ | 530/350 |

FOREIGN PATENT DOCUMENTS

| | | |
|---|---|---|
| B-39102/85 | 9/1985 | Australia . |
| 0 159779B1 | 6/1991 | European Pat. Off. . |
| 0517367A1 | 12/1992 | European Pat. Off. . |
| WO92/00566 | 3/1992 | WIPO . |
| WO92/04453 | 3/1992 | WIPO . |
| WO95/14098 | 5/1995 | WIPO . |

OTHER PUBLICATIONS

Leisner SM, et al. "Multiple domains exist within the upstream activator sequence of the octopine synthase gene." Plant Cell 1: 925–936, Sep. 1989.
Horsch RB, et al. "A simple and general method for transferring genes into plants." Science 227: 1229–1231, 1985.
Guevara–Garcia A, et al. Tissue–specific and wound–inducible pattern of expression of the mannopine synthase promoter is determined by the interaction between positive and negative cis–regulatory elements. Plant J. 4: 495–505, 1993.
An et al., *Mol. Gen. Genet.* 203: 245–50 (1986).
Anderson et al., *Phytopath.* 79: 1284–90.
Bandyopadhyay et al., *J. Biol. Chem.* 264: 19399–406 (1989).
Barker et al., *Plant Mol. Biol.* 2: 335–50 (1983).
Beachy et al., *Annu. Rev. Phytopathol.* 28: 451–74 (1990).
Benfey et al., *EMBO J.* 8: 2195–2202 (1989).
Benfey et al., *EMBO J.* 9: 1677–1684 (1990).
Benfey et al., *EMBO J.* 9: 1685–96 (1990).
Comai et al., *Plant Mol. Biol.* 15: 373–81 (1990).
Cuozzo et al., *Bio/technology* 6:549–57 (1988).
De Block et al., *EMBO J.* 6: 2513–18 (1987).
DiRita and Gelvin, *Mol. Gen. Genet.* 207: 233–41 (1987).
Ditta et al., *Proc. Nat'l Acad. Sci.* 77: 7347–51 (1980).
Duncan et al., *FEBS Lett.* 170: 59–63 (1984).
Ebert et al., *Proc. Nat'l Acad. Sci.* USA 84: 5745–49 (1987).
Ellis et al., *EMBO J.* 6: 11–16 (1987).
Ellis et al., *EMBO J.* 6: 3203–08 (1987).
Ellis et al., *Mol. Gen. Genet.* 195: 466–73 (1984).
Eggenberger et al., *J. Gen. Virol.* 70: 1853–60 (1989).
Fox et al. *Plant Mol. Biol.* 20: 219–33 (1992).
Guevara–Garcia et al., *Plant J.* 4: 495–505 (1993).
Gerlach et al., *Nature* 328: 802–05 (1987).
Ha et al., *Nucl. Acids Res.* 17: 215–23 (1989).
Harpster et al., *Mol. Gen. Genet.* 212: 182–90 (1988).
Hack et al., *Plant Physiol.* 65 : 949–55 (1980).
Hensgens et al., *Plant Mol. Biol.* 20: 921–38 (1992).
Hoekema et al., *Nature* 303: 179–80 (1983).
Horsch et al., *Science* 227: 1229–31 (1985).
Hemenway et al., *EMBO J.* 7: 1273–80 (1988).
Huisman et al., *J. Gen. Virol.* 69: 1789–98 (1988).
Kononowicz et al., *Plant Cell* 4: 17–27 (1992).
Koziel et al., *Biol/Technology* 11: 194–200 (1993).
Komro et al., *Plant Mol. Biol.* 4: 253–63 (1985).
Keen, *Plant Molec. Biol.* 19: 109–22 (1992).
Lam et al., *Proc. Nat'l Acad. Sci* USA 86: 7890–94 (1989).
Leung et al., *Mol. Gen. Genet.* 230: 463–74 (1991).
Langridge et al., *Proc. Nat'l Acad. Sci* 86: 3219–23 (1989).
Langridge et al., *Proc. Nat'l Acad. Sci* 86: 7890–94 (1989).
Leisner et al., *Proc. Nat'l Acad. Sci* 85: 2553–57 (1988).
Leisner et al., *Plant Cell* 1: 925–36 (1989).
Mitra et al., *Mol. Gen. Genet.* 215: 294–99 (1989).
Peterson, *Analyt. Biochem.* 83: 346–56 (1977).
Perlak et al., *Proc. Nat'l Acad. Sci.* USA 88: 3342–28 (1991).
Saito et al., *Planta* 184: 40–46 (1991).

(List continued on next page.)

*Primary Examiner*—Douglas W. Robinson
*Assistant Examiner*—Amy J. Nelson
*Attorney, Agent, or Firm*—Foley & Lardner

[57] ABSTRACT

Chimeric regulatory regions and gene cassettes based upon *Agrobacterium tumefaciens* opine sythase genes are provided for expressing foreign genes in plants. Various upstream activating sequences from opine synthase genes like the mannopine synthase and the octopine synthase genes are operably linked with promoters (or promoters plus activating sequences), both of which are then operably linked to the foreign gene. These regions and cassettes permit expression levels and patterns that could not be obtained previously.

12 Claims, 9 Drawing Sheets

OTHER PUBLICATIONS

Sanger et al., *Plant Mol. Biol.* 14: 433–43 (1990).
Schulz et al., *Crit. Rev. Plant Sci.* 9: 1–15 (1990).
Shah et al., *Plant Molec. Biol.* 6: 203–11 (1986).
Shah et al., *Science* 233: 478–481 (1986).
Stalker et al., *Science* 242: 419–23 (1988).
Stalker et al., *J. Biol. Chem.* 260: 4724–28 (1985).
Teeri et al., *EMBO J.*, 8: 343–50 (1989).
Thompson et al., *EMBO J.* 6: 2519–23 (1987).
Wiegand et al., *Plant Molec. Biol.* 7: 235–43 (1986).
Wek et al., *Nucl. Acid. Res.* 13: 3995–4010 (1985).
Schimdt, *Science* 265: 739 (1994).
Last et al., *Theor Appl Genet.* 81: 581–588 (1991).
Dynan, *Cell* 58: 1–4 (1989).
Willmitzer, *TIG* 4: 13–18 (1988).
Fang et al., *The Plant Cell* 1: 141–150 (1989).
An et al., *Plant Physiol.* 88: 547–552 (1988).
An, *Plant Physiol.* 81: 86–91 (1986).
Feitelson et al., *Bio Technology* 10: 271–275 (1992).
Adang et al., *Plant Molecular Biology* 21: 1131–1145 (1993).
Bruce et al., *Proc. Natl. Acad. Sci.* 85: 4310–4314 (1988).
Gelvin et al., *Proc. Natl. Acad. Sci.* 79: 76–80 (1982).
Gurley et al., *Proc. Natl. Acad. Sci.* 76: 2828–2832 (1979).
Bouchez et al., *EMBO Journal* 8: 4197–4204 (1989).
Singh et al., *Proc. Natl. Acad. Sci.* 86: 3733–3737 (1989).
Golemboski et al., Proc. Natl. Acad. Sci. 87: 6311–6315 (1990).
Broglie et al., Transgenic Plants 1: 265–276 (1993).
Hilder et al., Transgenic Plants 1: 317–338 (1993).

pMAS

Construct Number

1

2

MAS UAS

5

OCS UAS  MAS UAS

6

OCS UAS  MAS UAS

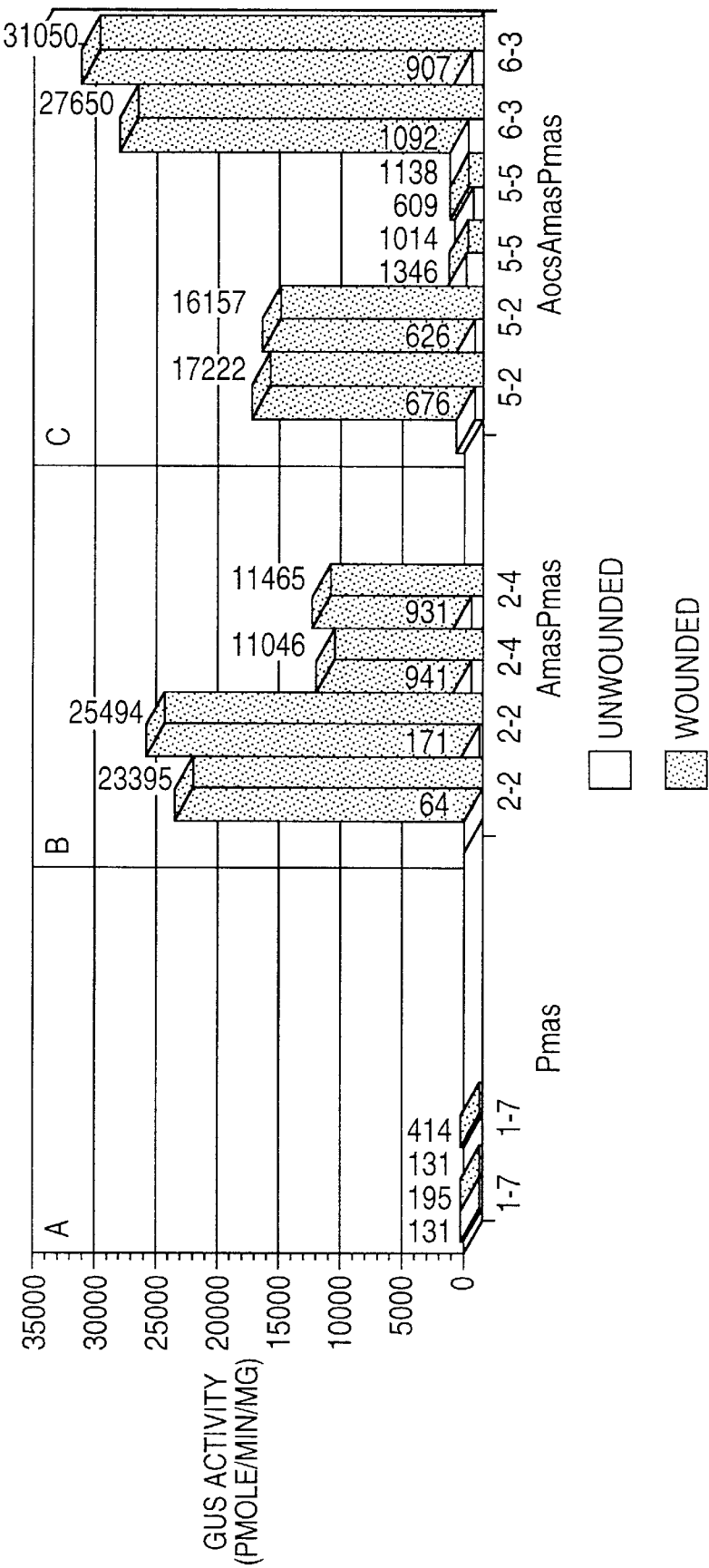

CHIMERIC REGULATORY REGIONS AND GENE CASSETTES FOR EXPRESSION OF GENES IN PLANTS

This Application is a Continuation-in-Part of application Ser. No. 08/155,067, filed Nov. 19, 1993, now abandoned.

BACKGROUND OF THE INVENTION

The present invention relates to chimeric regulatory regions useful for controlling the expression of genes in plants. These chimeric regulatory regions can be derived from the opine synthase genes of the plant pathogen *Agrobacterium tumefaciens*.

*Agrobacterium tumefaciens* is a Gram-negative soil bacterium that infects most dicotyledonous and some monocotyledonous plants. An infection by *Agrobacterium tumefaciens* often results in the formation of crown gall tumors on the infected plant.

During the *A. tumefaciens* infection process, a defined DNA segment ("T-DNA") of the large tumor-inducing ("Ti") plasmid is transferred to a susceptible plant cell and integrated into the plant nuclear genome, whereby the T-DNA genes are expressed. Some T-DNA genes encode enzymes involved in the synthesis of hormones that are active in plants. These hormones can cause tumors in infected plants. Other T-DNA genes direct the synthesis and secretion of unique amino acid and sugar derivatives, termed opines. *Agrobacterium tumefaciens* can utilize these opines as a carbon and sometimes a nitrogen source. See Gelvin, *Plant Physiol.* 92: 281–85 (1990); Gelvin, TRANSGENIC PLANTS (Academic Press 1993); Ream, *Ann. Rev. Phytopathol.* 27: 583–618 (1989); Zambryski, *Ann. Rev. Plant Physiol. Plant Mol. Biol.* 43: 465–90 (1992).

T-DNA genes contain regions that are functional in plant environments and possess similarities to plant regulatory regions. For example, most plant promoters contain cis-acting elements such as upstream activating sequences ("UAS") (often called "enhancers") that, by binding trans-acting factors, define or influence the promoter strength and tissue-specific expression pattern. Atchison, *Annu. Rev. Cell Biol.* 4: 127–53 (1988). The overall strength of a given promoter, as well as its pattern of expression, can be influenced by the combination and spatial orientation of cis-acting elements and the presence of the nuclear factors that interact with these elements. Dynan, *Cell* 58: 1–4 (1989). Although initially resident on a prokaryotic plasmid, T-DNA genes possess all of the sequence elements (promoters and UAS) required for transcription in plants. For instance, T-DNA genes contain TATA boxes that set the site of transcription initiation, and often contain upstream elements, located more than 100 bp from the transcription initiation site, that modulate the levels of transcription. See Gelvin, TRANSGENIC PLANTS (Academic Press 1993).

Two T-DNA genes that possess upstream activating sequences are the octopine synthase (ocs) and mannopine synthase (mas) genes. The ocs gene encodes a product that condenses arginine and pyruvate to form octopine. Hack and Kemp, *Plant Physiol.* 65: 949–55 (1980). A 16-base pair palindrome located upstream of the ocs gene is capable of activating a heterologous maize adh1 promoter in a transient expression system. Ellis et al., *EMBO J.* 6: 11–16 (1987); Ellis et al., *EMBO J.* 6: 3203–08 (1987). This palindrome is also essential for ocs promoter activity in stably transformed tobacco calli. Leisner and Gelvin, *Proc. Nat'l Acad. Sci. USA* 85: 2553–57 (1988); Leisner and Gelvin, *Plant Cell* 1: 925–36 (1989).

The mas 1' and 2' genes share a dual bidirectional promoter and a 479 bp intergenic region. These genes encode enzymes for a two-step pathway for the synthesis of mannopine. Ellis et al., *Mol. Gen. Genet.* 195: 466–73 (1984); Komro et al., *Plant Mol. Biol.* 4: 253–63 (1985). The transcription of the mas genes is divergent, and the intergenic region contains all the cis-acting elements necessary for the transcription of both genes. DiRita and Gelvin, *Mol. Gen. Genet.* 207: 233–41 (1987); Fox et al. *Plant Mol. Biol.* 20: 219–33 (1992); Leung et al., *Mol. Gen. Genet.* 230: 463–74 (1991); Guevara-Garcia et al., *Plant J.* 4: 495–505 (1993).

The ocs and mas gene promoters have been used to direct the expression of linked genes in transgenic plants. However, the application of these promoters has been restricted by weak expression levels in certain tissues of transgenic plants. DiRita and Gelvin, supra; Harpster et al., *Mol. Gen. Genet.* 212: 182–90 (1988); Sanger et al., *Plant Mol. Biol.* 14: 433–43 (1990). For example, the ocs promoter directs a distinct cell-specific pattern of expression in transgenic tobacco. Kononowicz et al., *Plant Cell* 4: 17–27 (1992). The mas gene exhibits weak expression in leaves and stems, but has stronger expression in roots and exhibits a degree of wound and auxin inducibility. Langridge et al., *Proc. Nat'l Acad. Sci* 86: 7890–94 (1989); Teeri et al., *EMBO J.*, 8: 343–50 (1989); Saito et al., *Planta* 184: 40–46 (1991); Guevara-Garcia et al., loc. cit.

Because promoters and other regulatory regions exhibit varying strengths and tissue specificities, certain recombinant regulatory regions have been developed. For example, enhancer elements that specifically bind certain trans-acting factors can modulate the transcriptional activity and the cell-specific expression pattern. Bienz and Pelham, *Cell* 45: 753–60 (1986).

The use of certain constitutive promoters, such as cauliflower mosiac virus (CaMV) 35S constructs, is also known. The CaMV 35S promoter has activators with multiple domains that can function to activate the 35S promoter in a developmentally and tissue-specific manner. See Benfey et al., *EMBO J.* 8: 2195–2202 (1989); Benfey, et al. *EMBO J.* 9: 1677–1684 (1990); Benfey et al., *EMBO J.* 9: 1685–96.

Koziel et al., *Bio/Technology* 11: 194–199 (1993) generally relates to promoters used in a promoter stacking construction in an effort to obtain tissue-specific promotion of a heterologous gene. Koziel shows construction of a gene expression system comprising a truncated cryIA(b) gene (the gene fragment used encodes the first 648 amino acids of an 1155 amino acid insecticidal protein from *Bacillus thuringiensis*) connected to either a CaMV 35S promoter or to a combination of two tissue-specific promoters derived from corn (phosphoenol-pyruvate carboxylase ("PEPC") promoter and a pollen specific promoter). Koziel reports high levels of expression from either promoter configuration. Koziel et al. also used (1) the PEPC promoter known to cause green tissue-specific expression and (2) a maize pollen-specific promoter. The expression of the insecticidal protein ranged from 1500–4000 ng/mg protein observed which appears to be a quite high level of expression. Additionally, use of the PEPC/pollen-specific promoters resulted in tissue-specific expression.

Others have attempted recombinant expression by other techniques. Bevan et al., PCT/GB92/00566 (1992), generally relates to a non-stacking application of a single promoter, which is different from the promoter of Koziel et al., to obtain tissue specific expression of a heterologous gene. This application apparently relates to the use of the bean phenylalanine ammonia lyase ("PAL") promoter to provide tissue-specific expression. A hybrid gene was constructed which fused the "putative transcriptional regulatory regions" of a genomic clone of PAL (that is, a clone which contains in addition to the coding sequences, intervening sequences which are part of the PAL gene sequence) and an open reading frame ("ORF") comprising 68 amino acids of the amino-terminal PAL protein with the entire ORF of β-glucuronidase ("GUS") followed by a polyadenylation and transcriptional termination region of nopaline synthase (the later two elements are typically fused in most eukaryotic plant expression vectors to ensure efficient expression). While this initial construct did exhibit strong activity in some plants, the researchers thereafter created deletions in the PAL promoter regions of the hybrid gene. The minimum PAL promoter necessary for full expression was found to be 253 base pairs from the transcriptional start site of PAL. By varying the deletion patterns chiefly within this minimal region, the researchers found that tissue-specific expression could be modified to a degree.

U.S. Pat. No. 5,034,322 generally relates to use of nopaline synthase promoters with a ribulose-1.5-bis-phosphate carboxylase small subunit gene.

It has also been reported that a chimeric promoter called "Mac," which incorporates the mas region from +65 to −301 and the 35S enhancer region from −90 to −941, shows GUS activity at a level several times that of a double CaMV 35S promoter in transgenic tobacco plants Comai et al., *Plant Mol. Biol.* 15: 373–81 (1990).

The above-described constructs have exhibited several limitations in terms of expression efficiency and controllability. For example, prior approaches have failed to provide strong expression in a constitutive-like manner in circumstances where such expression is desired.

SUMMARY OF THE INVENTION

It is therefore an object of the present invention to provide chimeric regulatory regions for improved expression of genes in plants.

It is another object of the present invention to provide chimeric regulatory regions that comprise promoters and upstream activating sequences from *Agrobacterium tumefaciens*.

It is still another object of the present invention to provide gene cassettes containing genes to be expressed under control of chimeric regulatory regions that comprise promoters and upstream activating sequences from *Agrobacterium tumefaciens*.

It is yet another object of the present invention to provide for the inducible expression of foreign genes in plants.

It is further object of the present invention to provide plasmids and transgenic plants containing gene cassettes.

In accomplishing these and other objects, there are provided, in accordance with one aspect of the present invention, chimeric regulatory regions for expressing genes in plants comprising an upstream activating sequence derived from a first *Agrobacterium tumefaciens* opine synthase gene operably linked to a promoter derived from a second *Agrobacterium tumefaciens* opine synthase gene that is different from the first *Agrobacterium tumefaciens* opine synthase gene. The first and second *Agrobacterium tumefaciens* opine synthase genes are preferably the mannopine synthase gene or the octopine synthase gene.

In accordance with another aspect of the present invention, there are provided chimeric regulatory regions for expressing genes in plants comprising at least two *Agrobacterium tumefaciens* opine synthase upstream activating sequences operably linked to a *Agrobacterium tumefaciens* opine synthase promoter. The upstream activating sequences can be derived from the same or different *Agrobacterium tumefaciens* opine synthase genes, such as mannopine synthase and octopine synthase. Additionally, one or both of the upstream activating sequences and the promoter can be derived from the same *Agrobacterium tumefaciens* opine synthase gene.

In accordance with yet another aspect of the present invention, there are provided gene cassettes containing a gene to be expressed operably linked to a chimeric regulatory region, as described above. A gene cassette also can include transcription terminators and polyadenylation signals, such as the nopaline synthase polyadenylation signal.

In accordance with yet another aspect of the present invention, there is provided a cassette for inducible expression of a foreign gene comprising a foreign gene operably linked to a regulatory region comprising a promoter derived from a mannopine synthase gene of *Agrobacterium tumefaciens* and an upstream activating sequence derived from a mannopine synthase gene of *Agrobacterium tumefaciens*. The regulatory region can also comprise an upstream activating sequence derived from an octopine synthase gene of *Agrobacterium tumefaciens*.

In accordance with still another aspect of the present invention, there are provided methods of expressing genes in a plant, comprising the steps of linking a gene to a chimeric regulatory region according to the present invention; inserting the gene and the chimeric regulatory region into a plant; and allowing the plant to express the gene.

In accordance with still another aspect of the present invention, there are provided plasmids and transgenic plants comprising chimeric regulatory regions and gene cassettes of the present invention.

Other objects, features and advantages of the present invention will become apparent in view of discussion, data and figures contained herein.

BRIEF DESCRIPTION OF THE FIGURES

FIG. 9 depicts nematode-induced GUS activity in various transgenic plants. Panel A is for transgenic plants that have the Pmas promoter but lack an activating sequence. Panel B is for transgenic plants that have a AmasPmas Promoter. Panel C is for transgenic plants that have a AocsAmasPmas Promoter.

DETAILED DESCRIPTION OF PREFERRED EMBODIMENTS

Figure 1:
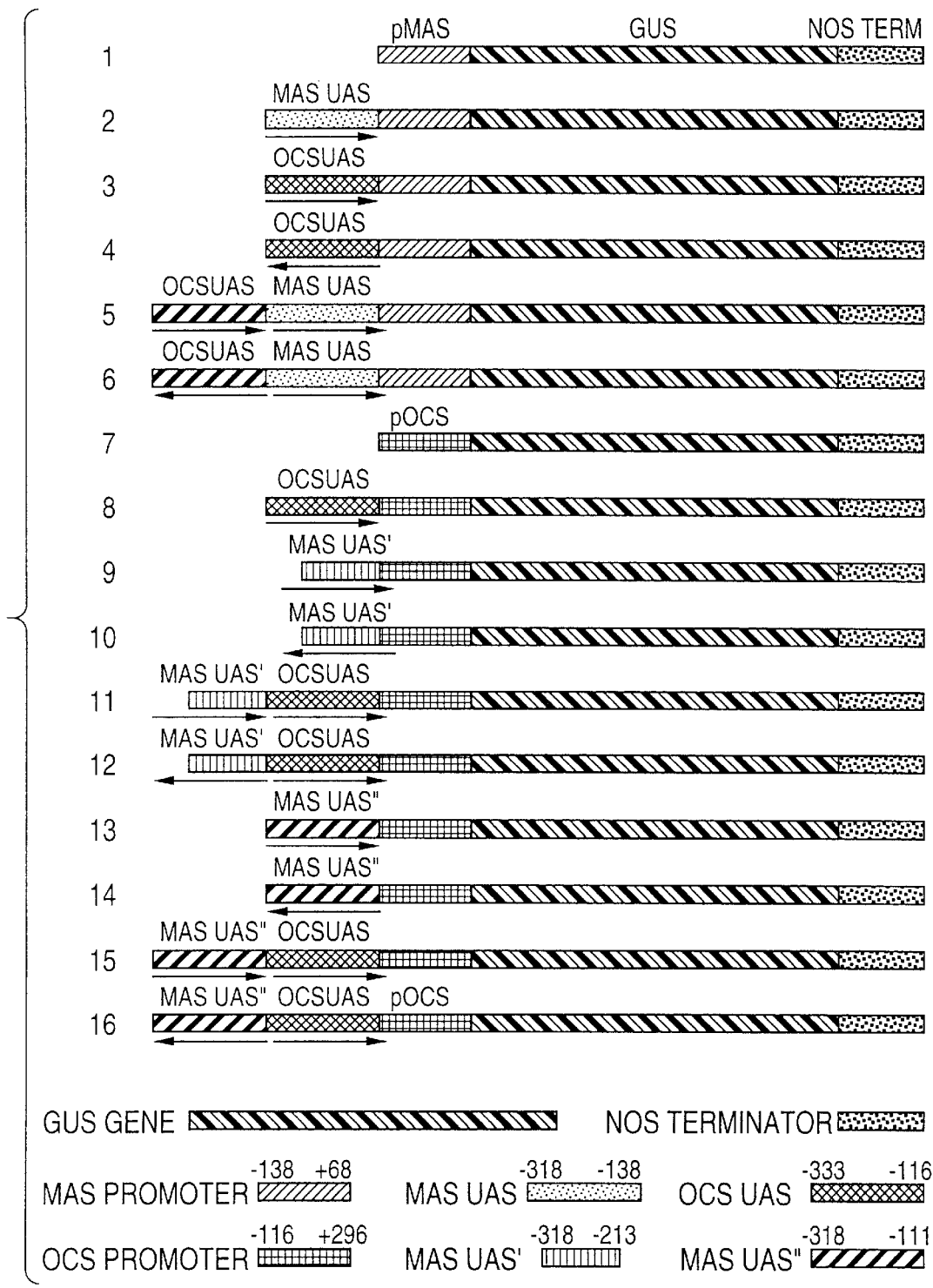
FIG. 1 depicts schematically the structure of chimeric mas and ocs based regulatory regions. Arrows indicate the orientation of the upstream activating sequence relative to the mas or ocs promoters. Numbers indicate nucleotide position relative to transcription initiation sites. A trimer of the ocs upstream activating sequence was used in constructs 3 and 4. A monomer or trimer of the ocs upstream activating sequence were used in constructs 5 and 6.

The present invention relates to chimeric regulatory regions comprising various upstream activating sequences and promoters from *Agrobacterium tumefaciens* opine synthase genes useful for controlling expression of foreign genes. A foreign gene includes any DNA that is sought to be expressed in the transgenic plant. In this context, the gene, no matter the source, is inserted into the plant genome and is thus foreign to that plant in the location of insertion, even if the gene originated from the plant being transformed. Inventive constructs according to the present invention are also disclosed in U.S. application Ser. No. 08/155,067, filed Nov. 19, 1993, which is incorporated by reference.

Any type of gene-encoded product is amenable to the present invention. Foreign genes to be expressed in transgenic plants with the present invention include but are not limited to βglucuronidase; genes encoding insecticidal and fungicidal toxins; pathogen resistance compounds; hypersensitive response compounds, such as peroxidases, glucanases and chitinases, as well as phytoalexins; pesticide, herbicide and fungicide tolerance genes; plant enzymes, such as those related to protein, starch, sugar and fat content; plant enzyme inhibitors such as protease and amylase inhibitors; plant hormones; insect hormones and pheremones; pharmaceutical and nutritional compounds, such as β-carotone; vitamins and antibodies, including fragments and single-chain derivatives of antibodies; and antisense transcripts to interfere with nucleotide sequences present within the plant. See, e.g., Kung and Wu, TRANSGENIC PLANTS, vol. 1 (Academic Press 1993).

In general, the native mannopine synthase promoter plus activating sequence, or the native octopine synthase promoter plus activating sequence, is relatively weak in the tissues of transgenic tobacco plants (GUS activity from linked gusA reporter genes is a few hundred to a few thousand GUS activity units). In accordance with the present invention, stacking the UAS from these genes upon a promoter plus activating sequence markedly increases the GUS activity from a linked gusA gene up to two orders of magnitude, resulting in activities up to hundreds of thousands of GUS activity units. Histochemical examination of the tissues of transgenic tobacco plants expressing these inventive promoter-gusA fusion genes reveals that the novel promoter and activating sequence combinations according to the invention function in most plant cell types. Thus, these combinations (chimeric regulatory regions) can be much more constitutive than the promoters known previously in the art.

The invention relates to improved plant regulatory regions capable of strong and continual promotion of gene expression. Additionally, tissue-nonspecific and/or tissue-enhanced expression can be obtained. Choice of activating sequences and promoters in accordance with the invention will yield the desired type of expression.

The inventive chimeric regulatory regions have demonstrated stronger expression characteristics in tobacco than any other known regulatory region. Tobacco is perhaps the widely employed model for plant transformation. In addition, the inventive regulatory regions can be nearly-constitutive (permanently turned on) and potentially useful in a greater number of plant tissues than the regulatory regions of the prior art.

The invention relates to a chimeric regulatory region for gene expression in plants, which can comprise an upstream activating sequence derived from a first *Agrobacterium tumefaciens* opine synthase gene, operably linked to a promoter sequence derived from a second *Agrobacterium tumefaciens* opine synthase gene or to an upstream activating and promoter sequence derived from a second *Agrobacterium tumefaciens* opine synthase gene.

The chimeric regulatory regions according to the invention can be operably linked to a foreign gene sequence, which can be operably linked to a plant-functional terminator sequence and then operably linked to a plant-functional polyadenylation signal sequence. The chimeric regulatory region according to one aspect of the invention will in many instances be highly constitutive.

An upstream activating sequence is a sequence which in the native state is usually at least 100 base pairs in advance of the native transcriptional start site, and can exert influence on expression. The UAS of octopine and mannopine synthase genes are particularly useful in this regard. These UAS can then be operably linked to a promoter sequence or to an upstream activating sequence and promoter sequence derived from a different *Agrobacterium tumefaciens* opine synthase gene.

The term "derived" when used in the context of DNA regions like promoters and upstream activating sequences refers to situations where the DNA region that is "derived" is obtained from or based upon a naturally-occurring DNA region or other source DNA region. The DNA region that is "derived" can differ, usually through deliberate mutation, from the naturally-occurring DNA region or other source DNA region.

The phrase "operably linked" refers to a first sequence(s) being positioned sufficiently proximal to a second sequence (s) so that the first sequence(s) can exert influence over the second sequence(s) or a region under control of that second sequence. For instance, an UAS can be operably linked to a promoter, whereby the UAS enhances the transcriptional strength of the promoter. In this situation, the UAS would typically be 5' to the promoter. The UAS and promoter can, in turn, be operably linked to a gene so that the gene will be expressed under the control of the UAS/promoter combination, which would typically be 5' to the gene. Usually, a promoter would be within about 30–50 base pairs from the start site of transcription and within a few hundred base pairs from the start site of translation. An activating sequence is usually within a few hundred base pairs of a promoter. For example, most activating sequence are within about 300 to 400 base pairs of the promoter that is enhanced. In embodiments of the invention where more than one activating sequence is employed, the activating sequences are usually within about 100 to 200 base pairs of each other.

A chimeric regulatory region according to the invention can be constructed wherein the source opine synthase genes are different from each another, and are preferably selected from the group of opine synthase genes consisting of mannopine, octopine, nopaline, and agropine synthase genes.

The expression of GUS activity directed by the native mas and ocs promoters plus activating sequences is limited to specific cell types. Operably linking an ocs activating sequence to the mas promoter plus activating sequence, as well operably linking a mas activating sequence to the ocs promoter plus activating sequence, has demonstrated a modulated expression pattern when compared to native constructs. Thus, in accordance with another aspect of the invention, GUS expression, as well as other genes, can be obtained in a large number of cell types, including xylem vessels and leaf epidermal cells. On the other hand, limited patterns of expression also can be obtained according to another aspect of the invention. A chimeric regulatory region operably linking an ocs UAS and a mas minimal promoter yields diminished expression in leaf vascular tissue, and stem expression confined to the phloem tissue.

The invention also relates to a recombinant gene cassette encoding a foreign polypeptide. A recombinant gene cassette can comprise an upstream activating sequence derived from a first *Agrobacterium tumefaciens* opine synthase gene and a promoter sequence or upstream activating and promoter sequence derived from the different, second *Agrobacterium tumefaciens* opine synthase gene, all of which are operably linked to a foreign gene sequence. The foreign gene sequence of the construct can be operably linked to a plant-functional terminator sequence and/or a plant-functional polyadenylation signal sequence so that the terminator sequence and polyadenylation signal can exert influence over the gene or transcript of the gene. The terminator sequence and the polyadenylation signal would be 3' to the gene.

Another aspect of invention relates that promoter and upstream activating sequence combinations (regulatory regions) that are inducible by wounding or pest feeding. One combination developed (AmasPmas) is preferentially expressed in root tissue and induced upon pathogen attack while another (AocsAmasPmas) is more generally expressed, but is further induced by pest attacks. These expression systems would be useful for genes targeted to root pests, such as nematodes or fungi, and also will have applications against insect pests and leaf pathogens. For example, genes encoding nematocidal toxins and proteins that interfere with the nematode reproductive cycle can be used with the present invention.

Pathogen infestation induces the chimeric regulatory regions using the marinopine synthase promoter with either the mas or ocs activating sequences, as described above. A variety of genes useful for pathogen resistance are discussed in Keen, *Plant Molec. Biol.* 19: 109–22 (1992).

Transcriptional elements, such as promoters and upstream activating sequences, of the opine synthase genes can be readily obtained based upon available sequence information. For example, transcriptional elements for the octopine synthase genes are disclosed in Leisner et al., *Proc. Nat'l Acad. Sci USA* 85: 2553–57 (1988); Leisner et al., *Plant Cell* 1: 925–36 (1989).

Transcriptional elements for the mannopine synthase genes are disclosed in DiRita and Gelvin, supra, Fox et al., *Plant Molec. Biol.* 20: 219–33 (1992); Leung et al., *Mol. Gen. Genet.* 230: 463–74 (1991); Langridge et al., *Proc. Nat'l Acad. Sci USA* 86: 3219–23 (1989). Transcriptional elements for the nopaline synthase genes are disclosed in Ha et al., *Nucl. Acids Res.* 17: 215–23 (1989); Mitra et al., *Mol. Gen. Genet.* 215: 294–99 (1989); Ebert et al., *Proc. Nat'l Acad. Sci USA* 84: 5745–49 (1987) An. et al., *Mol. Gen. Genet.* 203: 245–50 (1986). Transcriptional control elements for the agropine synthase gene are disclosed in Bandyopadhyay et al., *J. Biol. Chem.* 264: 19399–406 (1989). Additionally, the overall sequence of a T-DNA is disclosed in Barker et al., *Plant Molec. Biol.* 2: 335–50 (1983).

Various expression levels and patterns can be obtained by following the teachings contained herein. The amount and pattern of expression obtained by a given embodiment can be evaluated by marker systems, such as gusA, which are described herein. The invention is further explained by the following examples. These examples, although illustrative of the invention, do not limit the invention in any way.

EXAMPLE 1

Addition of an ocs or mas upstream activating sequence to a mas or ocs promoter and activating sequence strongly elevates GUS expression Novel combinations of the mas and ocs promoters and upstream activating sequences were created as depicted in FIG. 1. Various subdomains of the mas UAS were tested because previous deletion analysis has shown that sequences within 138 bases upstream of the transcription initiation site are sufficient for accurate transcription initiation of a mas2'/nptII fusion gene in sunflower crown gall tissue. Sequences between −138 and −318, however, may also be involved in regulating the quantitative level of mas2' promoter activity. DiRita and Gelvin, *Mol. Gen. Genet.* 207: 233–41 (1987).

The mas UAS tested were: (i) UAS=−318 to −138; (ii) UAS'=−318 to −213; and (iii) UAS"=−318 to −111. See FIG. 1.

A first group of chimeric regulatory regions were constructed and affixed as transcriptional fusions, to an uidA (gusA) gene using two deletions of the mas promoter −318 and −138 base pairs from the transcription initiation site (constructs 1–6 of FIG. 1). The first set of chimeric regulatory regions contains (in either orientation) a monomer or a trimer of the ocs activating sequence (−116 to −333) upstream of the −138 mas promoter deletion (constructs 3 and 4 of FIG. 1). The second set of chimeric regulatory regions contains similar ocs activating sequence monomers or trimers upstream of the −318 mas promoter deletion (constructs 5 and 6 of FIG. 1). This ocs region contains a 16 base pair palindrome, as well as 5' and 3' modulator sequences, that are important in activating the ocs promoter in tobacco calli and plants when stably incorporated into the plant genome. Leisner and Gelvin, 1988 and 1989 supra; Kononowicz et al., *Plant Cell* 4: 17–27 (1992).

A second group of chimeric regulatory regions were constructed as translational fusions to an uidA gene based upon two ocs deletions at positions −333 and −116 from the transcription initiation site (constructs 8–16 of FIG. 1). Two mas upstream activating sequence regions were created. A short mas region containing sequence from −213 to −318 was used in constructs 9–12 of FIG. 1. A long mas region containing sequence from −111 to −318 was used in constructs 13–16 of FIG. 1. A short or long mas region was added upstream of the two ocs deletions.

The chimeric constructs were prepared as follows. The basis of all constructs was the binary vector pBI101.2 from Clontech. Plasmid pBI101.2 is based upon the replicon pRK290. Plasmid pBI101.2 contains T-DNA borders, a nos-nptII chimeric gene for kanamycin selection in plants, and a promoterless GUS gene followed by a polyadenylation signal. The mas promoter region was obtained from a EcoRV-XbaI fragment, which contains a region that is −138 to +65 relative to the transcription initiation site (base pairs 20128 to 20343) from pKan2-138. Barker et al., *Plant Mol. Biol.* 2: 335–50 (1983); DiRita and Gelvin, supra. The mas activating sequence and promoter region, −318 to +65 relative to the transcription initiation site (base pairs 20128 to 20513) from pKan2-318 were initially cloned into the SmaI-XbaI sites of CUp31 (a pUC13 derivative having a pUC13 backbone but containing a polylinker reading 5' to 3' as HindIII, PstI, SstI, SmaI, BamH1, XbaI). The resulting HindIII-XbaI restriction endonuclease fragments from CUp31 were subsequently recloned into the HindIII-XbaI sites of the multi-linker of pBI101.2, resulting in the plasmids pNi1 and pNi2 (constructs 1 and 2, respectively).

An ocs enhancer fragment from the plasmid pENΔ1 (Leisner and Gelvin (1988), supra) was provided with HindIII linkers. This fragment is −333 to −116 relative to the transcription initiation site (base pairs 13774 to 13991, Barker et al., supra), and was cloned as a trimer into the HindIII site of pNi1 upstream of the mas promoter in both orientations, which resulted in constructs 3 and 4 of FIG. 1. To create constructs 5 and 6, the same ocs activating sequence fragment was cloned as a trimer, or as a monomer, into the HindIII site of pNi2 upstream of the mas activating sequence plus promoter.

A BamHI-EcoRI fragment containing the ocs promoter region with part of the ocs structural gene, which is −116 to +296 relative to the transcription initiation site (base pairs 13774 to 13362), and a XbaI-EcoRI fragment containing the ocs activating sequence and promoter region, which is −333 to +296 relative to the transcription initiation site (base pairs 13991 to 13362) from pEN1 (Leisner and Gelvin, 1988 supra) were cloned into the BamHI-EcoRI and XbaI-EcoRI sites, respectively, of pBluescriptII SK+ (Stratagene). XbaI-EcoRV fragments from the resulting pBluescript derivatives were subsequently cloned into the XbaI-SmaI sites of pBI101.2, creating GUS translational fusions in the plasmids pLH3 (construct 7) and pNi3 (construct 8). A XhoI-HaeIII fragment containing a "short" mas activating sequence, −318 to −213 relative to the transcription initiation site (base pairs 20513 to 20407) from pKan2-318 was cloned into the XhoI-HincII sites of pUX13 (a pUC13 derivative containing the pUC13 backbone but with the SmaI site converted to a XhoI site). The resulting XhoI-HindIII fragment was made blunt using Klenow fragment, XbaI linkers added, and the fragment cloned in both orientations into the XbaI sites of pLH3 (creating constructs 9 and 10) and pNi3 (constructs 11 and 12). Similarly, a longer XhoI-MnlI mas activating sequence fragment, −318 to −111 relative to the transcription initiation site (base pairs 20513 to 20305) from pKan2-318 was made blunt using Klenow fragment. Linkers for XbaI were added, and the fragment cloned in both orientations into the XbaI sites of pLH3 (generating constructs 13 and 14) and pNi3 (generating constructs 15 and 16).

Each of the above constructs were subsequently transformed into *E. coli* DH5α grown at 37° C. in LB medium with kanamycin. Orientations of inserts were verified by restriction mapping. The plasmid pBI121 (Clontech), containing a 800 bp HindIII-BamHI fragment with the CaMV 35S promoter, was used as a control to compare the relative strengths of the chimeric regulatory regions.

Recombinant plasmids containing the inserts were mobilized into *A. tumefaciens* LBA4404 by a triparental mating procedure using *E. coli* MM294 harboring the mobilizing plasmid pRK2013. Hoekema et al., *Nature* 303: 179–80 (1983); Ditta et al., *Proc. Nat'l Acad. Sci.* 77: 7347–51 (1980). In LBA4404, the recombinant plasmids remain as independent replicons ("binary vectors"), which can be transferred to plants and thereafter integrated into the plant nuclear DNA. Other methods, such as electroporation, can also be used to transform *A. tumefaciens* cells with plasmids.

*Agrobacterium tumefaciens* transconjugants were selected on AB minimal medium plates containing 0.5% glucose, 10 $\mu$g/ml rifampicin, and 50 $\mu$g/ml kanamycin. Lichtenstein and Draper, DNA CLONING: A PRACTICAL APPROACH (Glover ed., Oxford-IRL Press 1986). The introduction of the mobilized plasmid into the recipient *A. tumefaciens* strain was verified by DNA blot analysis.

Leaf disks from six-week old sterile shoot tip cultures of *Nicotiana tabacum var.* Wisconsin 38 were transformed via *A. tumefaciens* containing the constructs using a leaf disk transformation method. Horsch et al., *Science* 227: 1229–31 (1985). Infected leaf disks were grown for three days on MS3+ medium in the absence of antibiotics. Disks were then transferred to fresh shoot induction medium containing 1250 mg/l carbenicillin and 200 mg/l kanamycin. Kononowicz et al. *Plant Cell* 4: 17–27 (1992). After four to five weeks, a single shoot from each leaf disk was transferred to root induction medium containing 500 mg/l carbenicillin and 50 mg/l kanamycin. After two weeks, the shoot tips were transferred into BGS medium (MS medium containing 1 mg/l folic acid, 10 mg/l indole acetic acid, and 30 mg/l kinetin) containing 50 mg/l kanamycin to maintain in vitro shoot tip cultures of each line.

The regenerated transgenic tobacco plants containing each of these constructs were examined for GUS activity. Small pieces of tobacco tissue were harvested from the fourth or fifth fully expanded leaves, nearby stems, and actively growing young roots when plants were at the 10 to 12 leaf stage. The tissues were ground in 200 µl extraction buffer and stored at −70° C. Jefferson and Wilson, PLANT MOLECULAR BIOLOGY (Gelvin & Schilperoot eds., Kluwer Acad. Press 1991). GUS activity was assayed according to Jefferson and Wilson using 10 µl extract (about 20 to 30 µg protein) and MUG (4-methylumbelliferyl-β-D-glucuronide) as substrate. The protein concentration was measured according to Patterson, Analyt. Biochem. 83: 346–56 (1977).

Individual transgenic plants containing the same construct exhibited a range of GUS activity (see FIGS. 2–5). However, by measuring GUS activity in a large number of plants containing the same construct, the relative strength of each chimeric regulatory region could be estimated. Because no difference in range of GUS activities could be detected using constructs in which the activating sequence elements were cloned in opposite orientations, the data from each two-member construct sub-group were pooled (3 and 4, 5 and 6, 9 and 10, 11 and 12, 13 and 14, and 15 and 16).

Figure 2A:
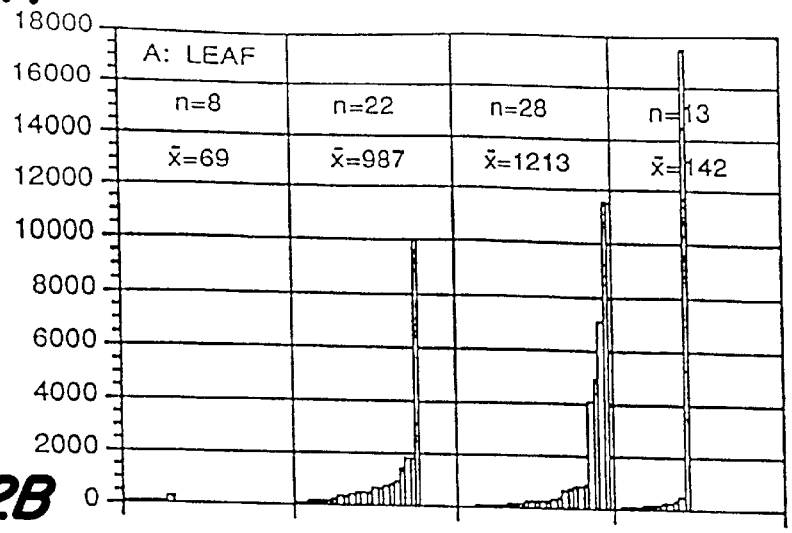
FIG. 2A–C depicts the GUS Activity of mas promoter-based constructs in extracts of tobacco primary transformants. GUS activity was assayed using total protein prepared from leaf (FIG. 2A), stem (FIG. 2B), or root (FIG. 2C) tissue. Each bar represents the activity of an individual transformant. The different constructs are as indicated at the bottom of the graph. The number of individual transgenic plants assayed for each construct is represented by "n." The average GUS activity for each construct is represented by an "$\bar{x}$." A=activating sequence; P=promoter; (Aocs)$_3$ =trimer of the ocs activating sequence.
Figure 2B:
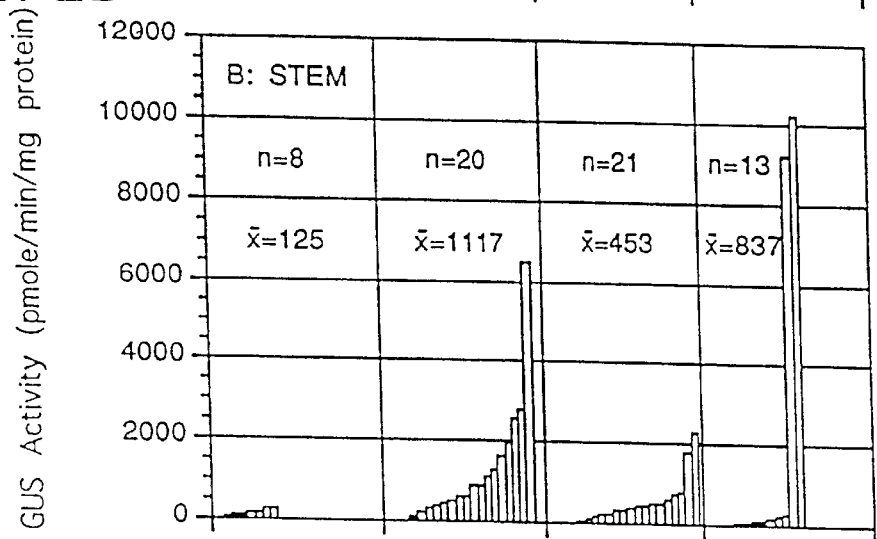
Figure 2C:
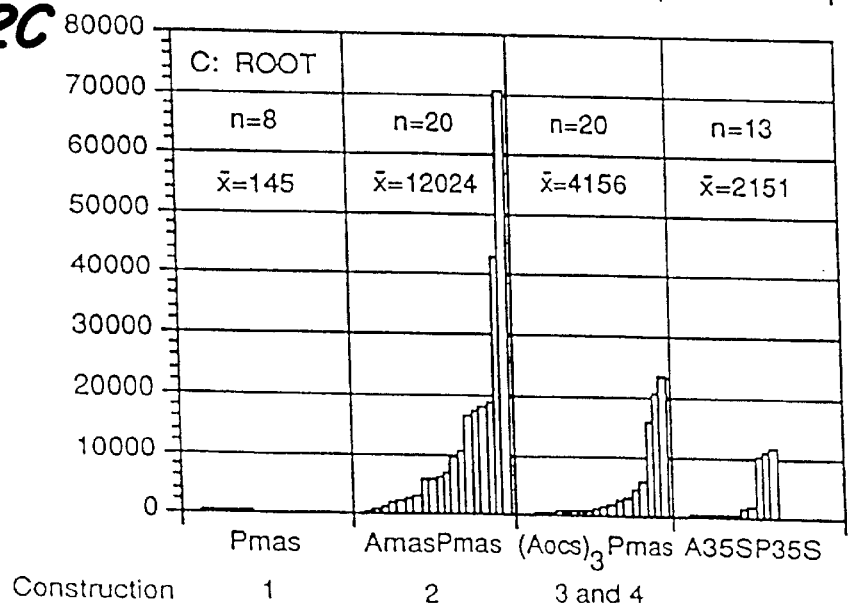
Figure 3A:
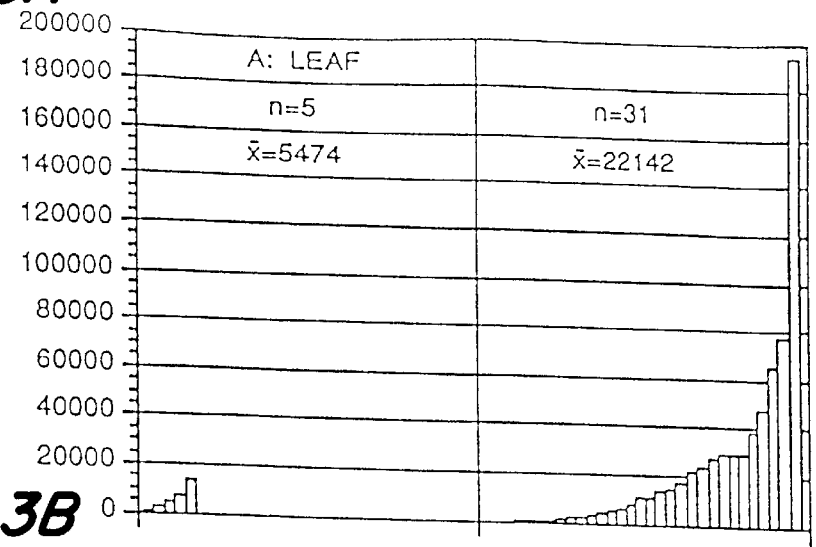
FIGS. 3A–C depicts the GUS Activity of mas promoter plus activating sequence based constructs in extracts of tobacco primary transformants. GUS activity was assayed using total protein prepared from leaf (FIG. 3A), stem (FIG. 3B), or root (FIG. 3C) tissue. Each bar represents the activity of an individual transformant. The number of individual transgenic plants assayed for each construct is represented by "n." The different constructs are as indicated at the bottom of the graph. The average GUS activity for each construct is represented by an "x." A=activating sequence; P=promoter; AocsAmasPmas=monomer of the ocs activating sequence linked to the mas activating sequence plus promoter; (Aocs)$_3$AmasPmas=trimer of the ocs activating sequence linked to the mas activating sequence plus promoter.
Figure 3B:
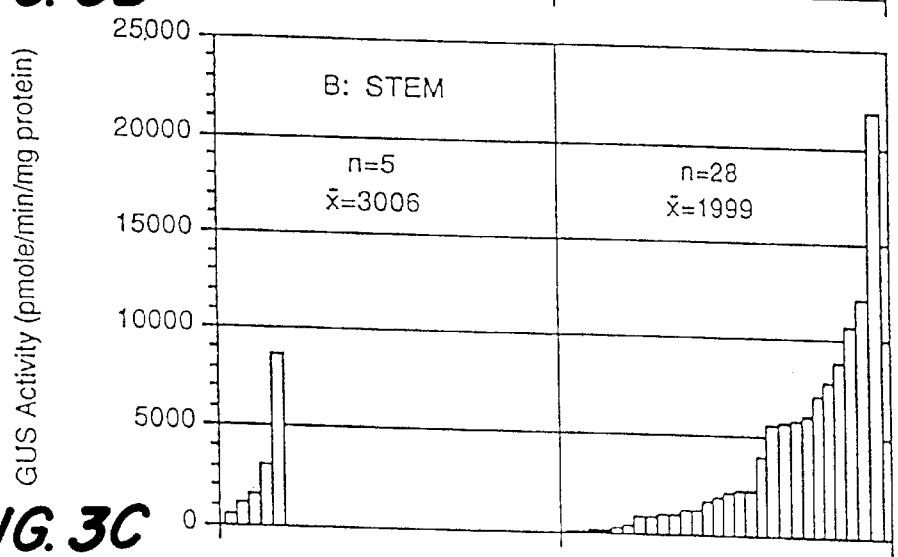
Figure 3C:
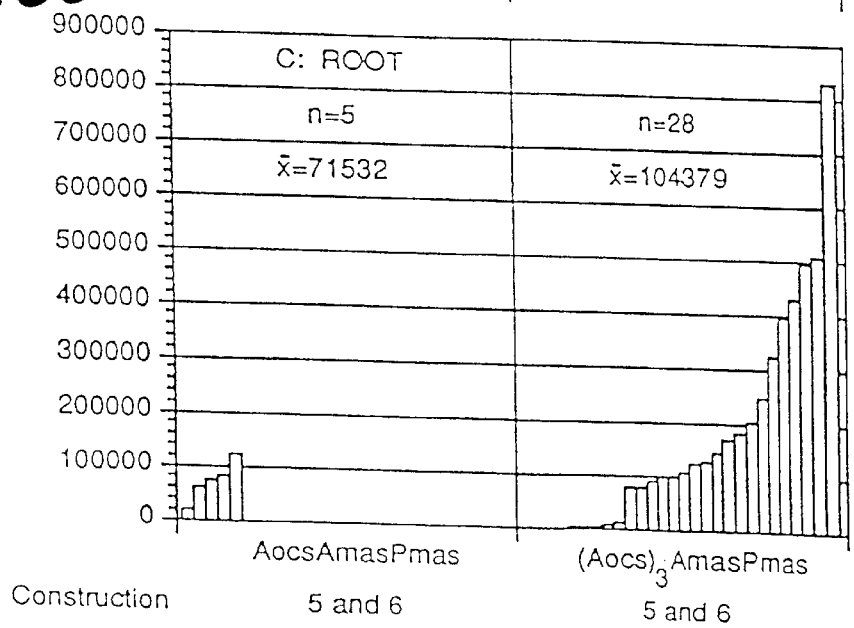

In all tissues examined, expression directed by the mas −138 deletion resulted in a minimal background level of GUS activity (FIGS. 2A–C, construct 1). Addition of the native mas activating sequence to the minimal mas promoter resulted in construct 2, which directed a low level of GUS activity in both leaf and stem tissues, averaging approximately 1000 units (FIGS. 2A and 2B). Relatively strong GUS activity in root tissue for this construct was observed, averaging approximately 12,000 units (FIG. 2C). These results indicate that this mas promoter and activating region accounts for the root-preferential expression of the mas2' promoter, discussed above. Replacement of the mas activating sequence with a heterologous ocs activating sequence (as a trimer) upstream of the −138 mas deletion (constructs 3 and 4) did not substantially alter the level of GUS activity relative to the homologous mas activating sequence and promoter combinations in both leaf and stem tissues (FIGS. 2A and 2B). Taken together with the data that indicates that the expression of the ocs activating sequence and promoter is not substantially higher in the root than in the leaf (see below, construct 8), the data suggest that the root-preferential expression of the mas promoter is conferred by an element within 138 bp of the mas transcription initiation site. The quantitative level of expression of this tissue-specific pattern can be further enhanced by either the ocs activating sequence or the mas activating sequence.

A homolog of the AS-1 tandem repeat motif (Lam et al., Proc. Nat'l Acad. Sci USA 86: 7890–94 (1989)) in the mas promoter region at position −66 has been identified. This element, when found in the CaMV 35S promoter, interacts with the transacting factor ASF-1 (Lam et al., loc. cit.) and has been stated to direct a tissue-specific expression pattern with high activity in roots (Benfey et al., supra).

The GUS activity directed by chimeric constructs was compared with activity obtained by the CaMV 35S promoter (−800 of pBI121). The majority of 35S-GUS transformants exhibited GUS activity similar to or lower than that of plants containing the mas activating sequence and promoter constructs (FIGS. 2A–C). As reported by Lam et al., supra, a root-preferential pattern of expression of the 35S promoter was observed.

Results indicate that the ocs and mas promoters contain cis-elements that direct transcription in a tissue-specific fashion. Kononowicz et al., Plant Cell 4: 17–27 (1992); Leung et al., Mol. Gen. Genet. 230: 463–74 (1991). In view of these results, combinations of heterologous activating sequences were tested to determine whether a combination could alter the expression pattern otherwise directed by the ocs or mas promoter alone, and thereby result in either elevated or diminished promoter activity in particular plant tissues. To test this hypothesis, constructs 5 and 6 depicted in FIG. 1, which include a trimer or a monomer of the ocs activating sequence placed upstream of the mas activating sequence and promoter, were introduced into tobacco and GUS activity was measured in different tissues (see FIGS. 3A–C). The new chimeric regions containing a monomer of the ocs activating sequence elevated the expression of GUS activity in leaf (6.6 fold), stem (3.0 fold) and root (3.4 fold) compared to the mas2' promoter and activating sequence (see FIGS. 2 and 3). Constructs containing a trimer of the ocs activating sequence strongly elevated the expression of GUS activity in leaf (22 fold), stem (1.7 fold) and root (9 fold) compared to the mas2' promoter and activating sequence (construct 2 of FIGS. 1 and 2A–C) lacking the extra ocs activating sequence. These results indicate that, at least in leaf and root tissue, the addition of multiple copies of the ocs activating sequence had a surprisingly powerful amplifying effect upon the relative activity of the mas2' promoter and activating sequence.

Assays indicated that the activity of the CaMV 35S promoter in the leaves of transgenic plants (averaging 200 pmole/min/mg protein) was comparable with the data of Comai et al., Plant Mol. Biol. 15: 373–81 (1990). Duplicating the 35S enhancer resulted in a two-fold increase in GUS activity in the leaves. Comparing the data from Comai et al., loc. cit. with the data obtained with the inventive constructs, the chimeric regions of constructs 5 and 6 directed respectively 156-fold and 26-fold stronger GUS expression in leaves than did the 35S promoter and the enhanced double 35S promoter, respectively.

Seed from T2 generation tobacco plants containing double 35S-GUS or Mac-GUS constructs were also tested. Measurements of GUS activity in the leaves of these transgenic plants confirmed the relative strengths of the promoters as discussed above. Table I below depicts average GUS activity in the leaves of transgenic tobacco plants harboring various promoter-uidA fusions.

TABLE I

| Promoter/Activating Sequence | Construct | GUS Activity (pmole/min/mg protein) |
|---|---|---|
| Pmas | 1 | 69[a] |
| AmasPmas | 2 | 987[a] |
| (Aocs)$_3$Pmas | 3 and 4 | 1213[a] |
| AocsAmasPmas | 5 and 6 | 5474[a] |
| (Aocs)$_3$AmasPmas | 5 and 6 | 22142[a] |
| Pocs | 7 | 0[a] |
| AocsPocs | 8 | 566[a] |
| Amas'Pocs | 9 and 10 | 66[a] |
| Amas'AocsPocs | 11 and 12 | 13957[a] |
| Amas"Pocs | 13 and 14 | 138[a] |
| Amas"AocsPocs | 15 and 16 | 1617[a] |
| CaMV 35S | | 142[a] |
| CaMV Double 35S | | 850[b] |
| Mac (A35SAmasPmas) | | 5230[b] |

[a]Average GUS activity among all primary transformants.
[b]Average GUS activity among the F1 progeny of a primary transformant expressing high GUS activity (Comai et al., supra).

Table II below shows the average GUS activity found in leaves of F1 generation transgenic tobacco plants harboring various promoter-uidA fusions.

TABLE II

| Promoter and Activating Sequence Combination | Construct Number[a] | GUS Activity (pmole/min/mg protein) | |
|---|---|---|---|
| | | 40 Days[b] | Soil |
| AmasPmas | 2-2 | 206 | 225 |
|  | 2-4 | 180 | 203 |
| Construct Average |  | 193 | 214 |
| (Aocs)₃AmasPmas | 5-2 | 398 | 3148 |
|  | 5-3 | 8297 | 3513 |
|  | 5-4 | 1555 | 1870 |
|  | 5-5 | 3836 | 23631 |
|  | 6-1 | 4616 | 774 |
|  | 6-2 | 779 | 1363 |
|  | 6-3 | 3628 | 933 |
| Construct Average |  | 3301 | 5033 |
| AocsPocs | 8-4 | 279 | 216 |
|  | 8-6 | 252 | 90 |
|  | 8-7 | 460 | 258 |
|  | 8-10 | 115 | 998 |
|  | 8-14 | 546 | 1460 |
| Construct Average |  | 330 | 604 |
| AmasAocsPocs | 11-1 | 621 | 975 |
|  | 11-2 | 194 | 169 |
|  | 11-3 | 1194 | 1033 |
|  | 11-6 | 615 | 1084 |
|  | 12-2 | 199 | 103 |
|  | 12-5 | 8949 | 5157 |
| Construct Average |  | 1962 | 1420 |
| CaMV3SS | 17-2 | 286 | 139 |
|  | 17-5 | 260 | 153 |
|  | 17-7 | 125 | 195 |
| Construct Average |  | 224 | 162 |

[a]The first number indicates the particular construct. The second number represents an individual primary transformant.
[b]Seeds of primary transformants were germinated on agar containing kanamycin, and small plantlets were transferred to medium containing kanamycin and assayed about 40 days later.

Figure 4A:
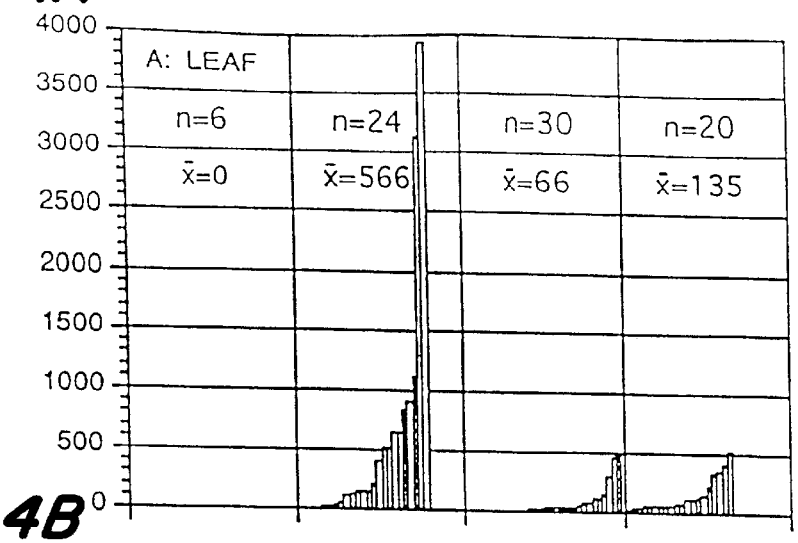
FIGS. 4A–C depicts the GUS Activity of ocs promoter-based constructs in extracts of tobacco primary transformants. GUS activity was assayed using total protein prepared from leaf (FIG. 5A), stem (FIG. 5B), or root (FIG. 4C) tissue. Each bar represents the activity of an individual transformant. The different constructs are as indicated at the bottom of the graph. The number of individual transgenic plants assayed for each construct is represented by "n." The average GUS activity for each construct is represented by "x̄." A=activating sequence; P=promoter; Amas'=mas region −213 to −318; Amas"=mas region −111 to −318.
Figure 4B:
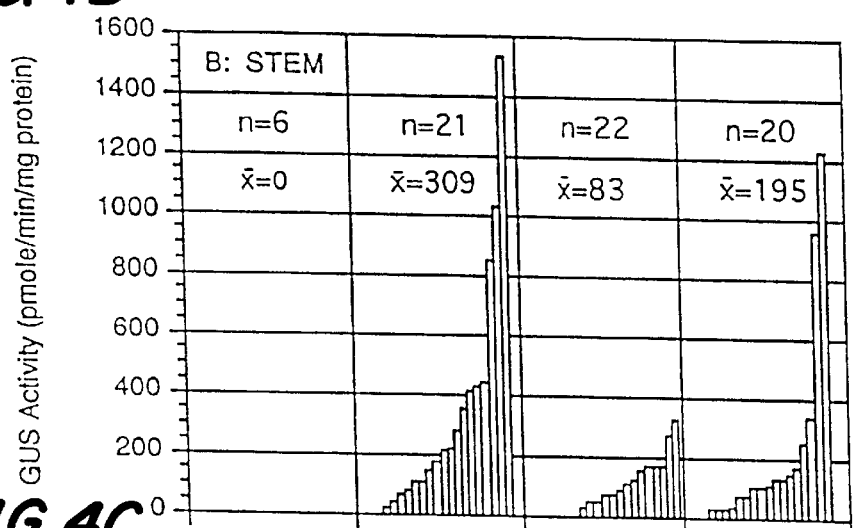
Figure 4C:
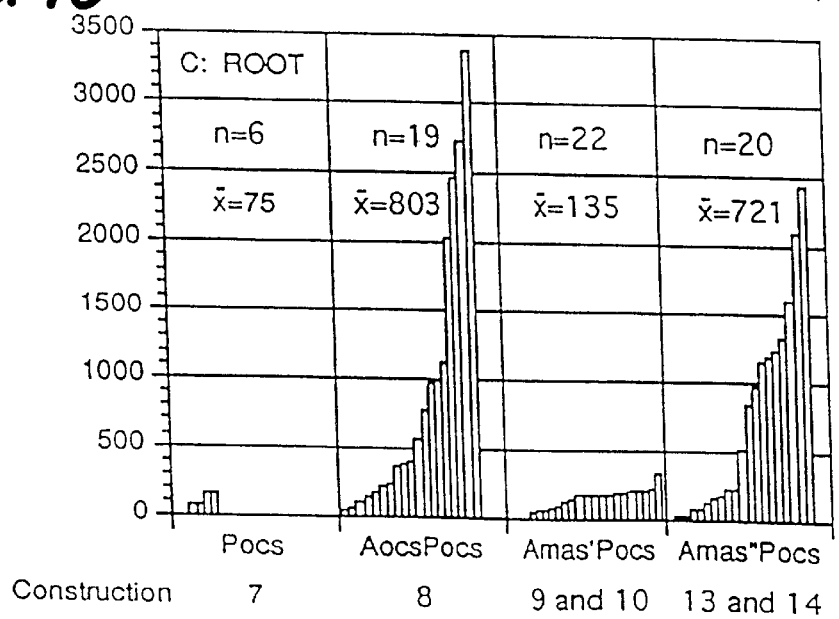
Figure 5A:
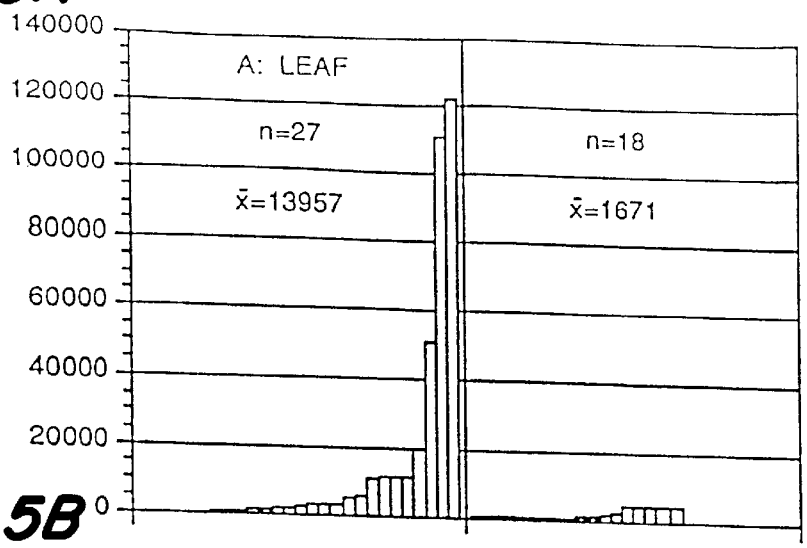
FIGS. 5A–C depicts the GUS Activity of ocs promoter plus activating sequence based constructs in extracts of tobacco primary transformants. GUS activity was assayed using total protein prepared from leaf (FIG. 5A), stem (FIG. 5B), or root (FIG. 5C) tissues. Each bar represents the activity of an individual transformant. The different constructs are as indicated at the bottom of the graph. The number of individual transgenic plants assayed for each construct is represented by "n." The average GUS activity for each construct is represented by "x̄." A=activating sequence; P=promoter; Amas'=mas region −213 to −318; Amas"=mas region −111 to −318.
Figure 5B:
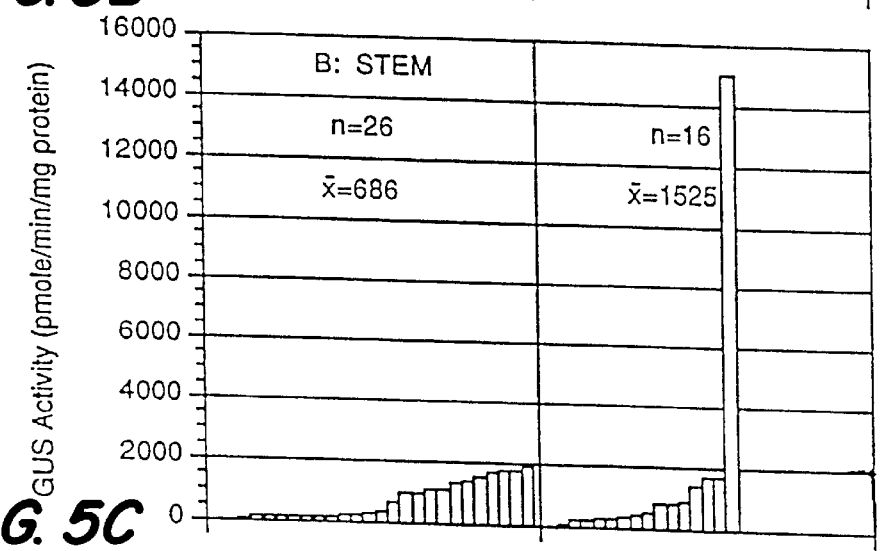
Figure 5C:
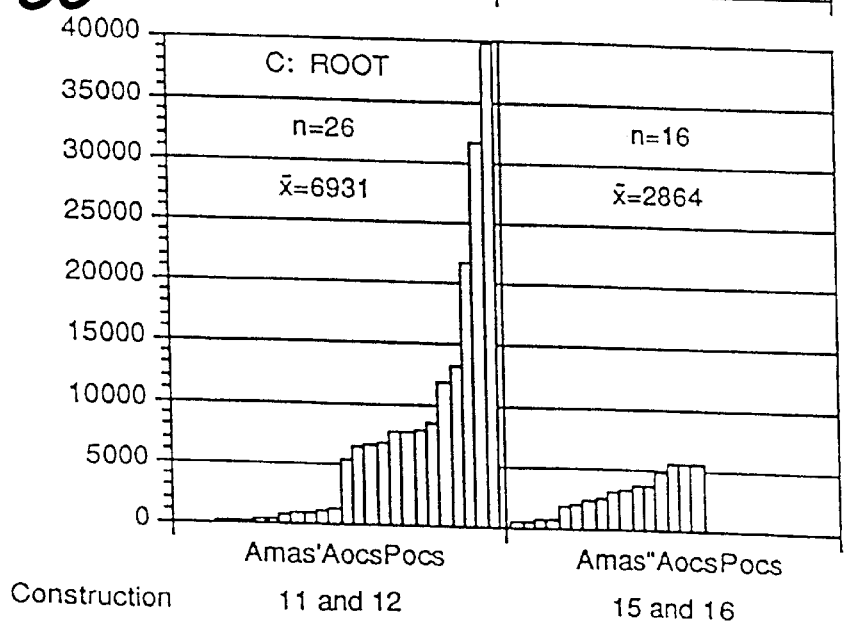

A series of chimeric constructs, based upon the ocs minimal promoter (−116 to +296), were tested to evaluate strengths and patterns of tissue-specific expression. As shown in FIGS. 4A–C, the ocs activating sequence and promoter (construct 8, FIG. 1) directed a low and relatively uniform level of GUS activity (averaging between 200 and 400 pmole/min/mg protein) in the leaf, stem, and root tissues of transgenic tobacco plants. Replacement of the ocs activating sequence with a short version of the mas activating sequence (from −213 to −318; constructs 9 and 10) resulted in a chimeric construct that directed only a low level of GUS activity in all tissues examined.

A longer version of the mas activating sequence (from −111 to −318) upstream of the minimal ocs promoter (constructs 13 and 14) was also tested. These constructs directed a slightly increased level of GUS activity, but only in root tissue. In addition to the AS-1 homologue found at −66, a sequence similar to the AS-1 element also exists at position −290. Although this sequence is also present in the short version of the mas activating sequence, other sequences between −213 and −103 apparently are necessary to direct root-preferential expression.

A short version of the mas activating sequence (−318 to −213; constructs 11 and 12) was next placed upstream of the ocs activating sequence plus promoter. Compared to a construct containing only the ocs activating sequence plus promoter (construct 8), these constructs directed 6-fold, 2.5-fold, and 15-fold increases in GUS activity in leaf, stem, and root tissues, respectively (see FIGS. 5A–C). The expression of these constructs was slightly root-preferential, suggesting a possible interaction of the AS-1-like element with the ocs activating sequence. Interestingly, constructs containing a longer version of the mas UAS (affixed to the ocs activating sequence and promoter; constructs 15 and 16) directed a slightly lower level of GUS activity than did constructs (11 and 12) containing the shorter mas activating sequence (see FIGS. 5A–C). Nevertheless, the "stacking" of both the ocs and mas activating sequences 5' to the mas promoter resulted in a large increase in promoter strength relative to the ocs activating sequence and promoter alone.

EXAMPLE 2
Correlation Between T-DNA Copy Number and GUS Activity in Transgenic Tobacco Plants To determine the relationship between T-DNA copy number and GUS activity, genomic DNA from 16 transgenic plants containing either construct 5 or construct 11 were analyzed. First, genomic DNA was extracted from plant tissues and digested to completion with HindIII. Rogers and Bendich, PLANT MOLECULAR BIOLOGY (Gelvin and Schilperoot eds., Kluwer Acad. Pub., 1992). Ten micrograms of DNA was digested with HindIII, the fragments separated by electrophoresis through a 1.0% agarose gel, and the DNA eluted onto a nylon membrane using a capillary transfer procedure. Maniatis et al., MOLECULAR CLONING: A LABORATORY MANUAL (Cold Spring Harbor 1982). Nucleic acids were fixed to the membrane by baking for 2 hours at 80° C. under vacuum. Prehybridization was conducted for 2–4 hr at 65° C. in 1.5x SSC (1xSSC is 0.15 M NaCl, 0.015 M Na citrate), 1.0% SDS, 0.5% Blotto, and 0.5 mg/ml sheared salmon sperm DNA.

Hybridization was performed at 65° C. overnight in fresh solution with a probe containing the GUS coding region sequence (an XbaI-SstI restriction endonuclease fragment from pBI101.2) that was labeled with $^{32}$P-dCTP. After completion of hybridization, the membrane was washed successively for 15 minutes at room temperature in the following solutions: 2xSSC/0.1% SDS, 0.5xSSC/0.1% SDS, 0.1xSSC/0.1% SDS. The final wash was done for 30 minutes with 0.1xSSC/1.0% SDS at 50° C.

Using this combination of restriction endonuclease and hybridization probe, the number of T-DNA copies could be estimated based on the number and intensity of hybridizing bands. The number of integrated copies varied from one to several in individual transformants. GUS activity did not correlate with the number of integrated uidA genes. For example, in certain instances a plant containing a single, integrated uidA gene exhibited considerably higher GUS activity in the leaves than did plants containing multiple, integrated copies of the uidA gene.

EXAMPLE 3
Correlation Between GUS Activity and uidA MRNA in Transgenic Tobacco Plants Because GUS activity was used as a measure of expression strength, it was necessary to verify that this activity reflected the steady-state level of uidA mRNA. This correlation is especially important because of a report that GUS activity did not correlate with uidA mRNA abundance when using the mas2' promoter and a uidA reporter gene. Hensgens et al., *Plant Mol. Biol.* 20: 921–38 (1992).

Accordingly, the steady-state level of uidA nRNA isolated from leaves of individual transgenic plants containing four different constructs (constructs 2, 5, 8, and 11) was examined. First, total RNA was isolated according to the procedure of de Vries et al., PLANT MOLECULAR BIOLOGY (Gelvin and Schilperoot eds., Kluwer Acad. Pub., 1992). Five milligram samples were fractionated by formaldehyde gel electrophoresis through a 1.2% agarose gel in MOPS/

EDTA buffer (50 mM MOPS, 1 mM EDTA, pH 7.0), followed by blotting onto a nylon membrane. The integrity of the RNA was checked by agarose gel electrophoresis and ethidium bromide staining. The fluorescence of the nucleic acids also served to verify that equal amounts of RNA were loaded in each lane. Hybridization conditions were as described above for genomic DNA analysis.

After completion of hybridization, the membrane was washed successively for 15 minutes at room temperature in the following solutions: 2× SSC/0.1% SDS, 0.5× SSC/0.1% SDS, 0.1× SSC/0.1% SDS. The final wash was done for 30 minutes with 0.1× SSC/1.0% SDS at 60° C.

The RNA blot analysis, using a hybridization probe derived from the GUS coding sequence, revealed a transcript of the expected size (approximately 2300 nucleotides). There was a close correlation between GUS activity and the steady-state level of uidA mRNA, which is contrary to the reports from Hensgens et al.

EXAMPLE 4

Modulation of Cell-Specific GUS Expression Patterns by Different Combinations of ocs and mas Promoters and Activating Sequences Histological examinations of transgenic tobacco tissues to determine the cell-specific patterns of GUS activity. These patterns of expression were revealed by histochemical staining of thin sections of plant tissue with X-gluc.

These histochemical studies were conducted according to Jefferson and Wilson, supra. Briefly, the plant materials were prefixed for 20–40 min with 0.1–0.3% formaldehyde, 0.1 M Triton X-100, 0.1 M phosphate buffer (pH 7.0), rinsed with 0.1 M phosphate buffer, and stained with 1-2 mM X-gluc (in 0.1 M Triton X-100, 0.1 M ETDA, 0.1 M phosphate buffer) for 2–14 hours. After refixation for two hours using 3–5% formaldehyde in 0.1 M phosphate buffer, the samples were cleared using 70% ethanol, embedded in paraffin, and sectioned (12–18 mm) using a rotary microtome. The tissue sections were counter-stained with 1.0% periodic acid-0.5% Schiff's reagent ("PAS").

There was no detectable GUS activity in any cell type of leaf tissue examined from plants containing the mas promoter but lacking an activating sequence (construct 1). Plants containing a chimeric uidA gene under the control of the native mas activating sequence plus promoter (construct 2) showed moderate GUS activity in leaf mesophyll (including palisade and spongy parenchyma) cells and guard cells, but no GUS activity was detected in epidermal cells. In vascular tissues, moderate staining was observed in xylem trachid cells, whereas relatively weaker staining was seen in phloem and ray parenchyma cells. A similar pattern of GUS activity was observed in leaf blades harboring a trimer of the ocs activating sequence and the mas promoter (constructs 3 and 4). However, in leaf vascular tissues GUS activity was greatly diminished in all cell types. "Stacking" a trimer of the ocs activating sequence upon the mas activating sequence plus promoter (construct 5 and 6) resulted in strong GUS activity not only in leaf mesophyll and guard cells, but also in epidermal cells. This result indicates that both the distal and proximal heterologous activating sequences interact to modulate the expression pattern. In leaf vascular tissues, the expression patterns were similar regardless of whether the trimeric ocs activating sequences were linked to the mas activating sequence plus promoter.

No GUS activity was detected in leaf tissues containing the minimal ocs promoter (construct 7). Expression of GUS activity directed by the ocs activating sequence plus promoter (construct 8) was similar to that of the mas activating sequence plus promoter in cross sections of the leaf blade. This pattern of GUS activity was also observed in leaf blades of plants in which the uidA gene was under the control of a chimeric promoter composed of a short mas activating sequence and the ocs activating sequence plus promoter (constructs 11 and 12). In leaf branch vascular tissue, the ocs activating sequence plus promoter also directed GUS expression, but only in trachid cells. In contrast to the mas activating sequence plus promoter, the ocs activating sequence plus promoter directed a moderate level of expression of GUS activity in ray and phloem cells and very weak expression in parenchyma and xylem trachid cells in the leaf main vascular tissues. A similar pattern of GUS activity was observed in leaf vascular tissue whether or not a short mas activating sequence was added to the ocs activating sequence plus promoter. However, activity was greatly increased in parenchyma, ray, and phloem cells. GUS activity was undetectable in plants containing a mas activating sequence linked to an ocs promoter (constructs 9 and 10).

The mas activating sequence plus promoter (construct 2) directed weak expression of GUS activity in the stalks of glandular trichomes, but strong expression in the heads. Operably linking a trimer of the ocs activating sequence to the mas activating sequence plus promoter (constructs 5 and 6) resulted in a similar pattern of expression; however, the relative level of GUS activity was strongly elevated in the stalk cells. The expression of GUS activity in trichomes directed by constructs containing a short mas activating sequence linked to an ocs activating sequence plus promoter (constructs 11 and 12) was strong in the heads of glandular trichomes, but weak in the stalk cells.

In the stems of transgenic plants, the mas activating sequence plus promoter (construct 2) directed weak expression of GUS activity in cortical cells. Strong GUS activity was observed in ray and phloem cells, but expression in xylem trachid cells was relatively weak. This pattern did not vary even if there were a trimer of the ocs activating sequence cloned upstream of the mas activating sequence plus promoter (constructs 5 and 6). When the mas activating sequence was replaced by a trimer of the ocs activating sequence (constructs 3 and 4), a different pattern was observed. Expression of GUS activity was still strong in phloem cells, but was now weak in ray and xylem trachid cells. In contrast to the mas activating sequence plus promoter, the ocs activating sequence plus promoter (construct 8) directed relatively weaker expression in ray and phloem cells, but strong expression in trachid cells. When a short mas promoter was added upstream of the ocs activating sequence plus promoter (construct 11), the pattern remained essentially the same.

GUS activity directed by the mas activating sequence plus promoter (construct 2) in root tissue was somewhat variable. In fact, there was a regenerated plant in which GUS activity could be detected in root cap cells, epidermal cells, and root hairs as well as root cortical, phloem, and xylem cells of the root maturation zone. However, little GUS activity was detected in the root elongation zone. GUS activity was frequently, but not always, detected in every cell type of the root maturation zone when an trimer of the ocs activating sequence was added to the mas activating sequence plus promoter (constructs 5 and 6). Replacement of the mas activating sequence with a trimer of the ocs activating sequence (constructs 3 and 4) resulted in GUS activity only in the peripheral root cortical and endodermal cells of the root elongation zone. Similar patterns of GUS activity were observed when either the ocs promoter and activating sequence (construct 8) or a short mas activating sequence plus the ocs activating sequence and promoter (constructs 11 and 12) directed expression of the uidA gene.

Figure 6A:
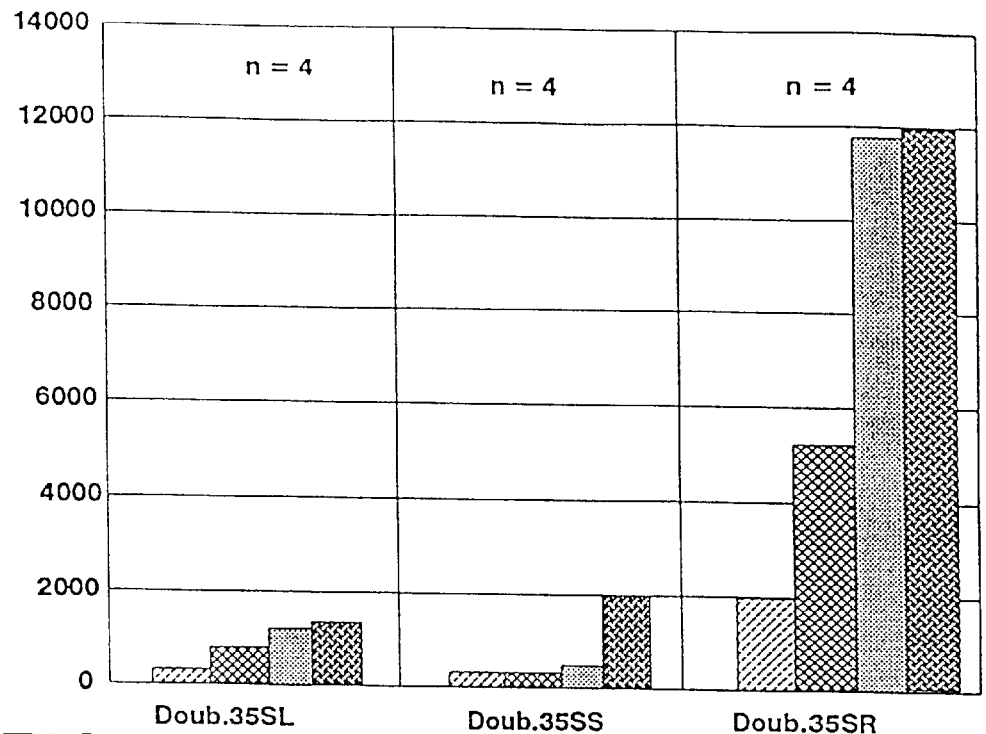
FIGS. 6A–B depicts approximate levels of expression of GUS activity of double CaMV 35S and Mac promoters in leaves (double 35SL, MacL), stems (double 35SS, MacS), and roots (double 35SR, MacR) of several transgenic tobacco plants.
Figure 6B:
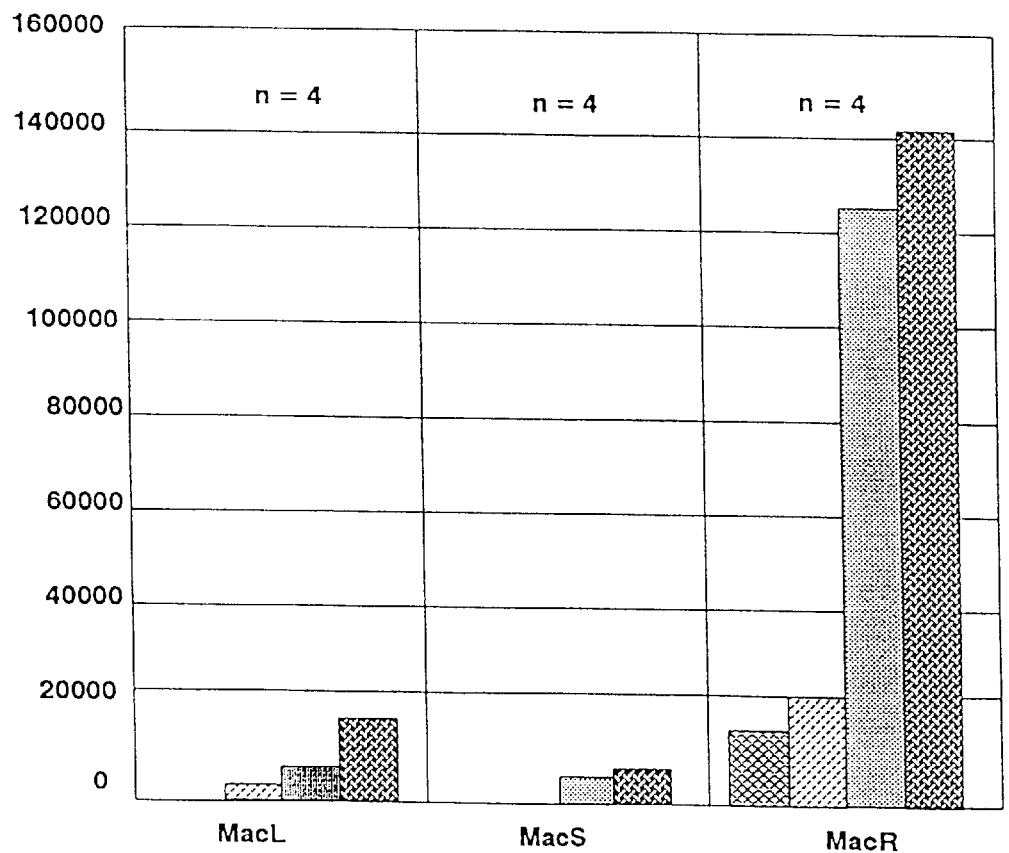

EXAMPLE 5
Comparison of the Inventive Chimeric Regulatory Regions to Other Regulatory Regions The activity of the mas activating sequence plus promoter is greatest in root tissues. Addition of a trimer of the ocs activating sequence to the mas activating sequence plus promoter increased the level of GUS activity 2- to 23-fold. This increase in activity is greatest in leaf tissue, but is also seen in stem and root tissues. The activity of the ocs activating sequence plus promoter is approximately equal in the leaves, stems, and roots of transgenic tobacco plants. Addition of a "short" version of the mas activating sequence to the ocs activating sequence plus promoter increased the level of GUS expression 2- to 20-fold. This increase in activity was greatest in leaf tissues. Combining multiple copies of the ocs activating sequence with the mas activating sequence plus promoter resulted in a transcriptional regulatory element that in leaves was approximately 156-fold stronger than the 35S promoter, 26-fold stronger than the "enhanced" double CaMV 35S promoter, and 4.2-fold stronger than the "Mac" and "Big Mac" promoters described in Comai et al., *Plant Mol. Biol.* 15: 373–81 (1990) (See FIGS. 2A–C and 3A–C and Table I). Data concerning the double 35S and Mac promoters for leaf ("L"), stem ("S") and root ("R") are presented in FIGS. 6A–B. It should be noted that the stronger activity of the chimeric promoters, represented by constructs 5 and 6, relative to the double CaMV 35S, Mac, and Big Mac promoters are minimal estimates. In addition, histochemical analysis of the cells of transgenic plants harboring these constructs revealed that these "stacked" activating sequences directed the expression of GUS activity in almost all cell types. For example, strong expression of GUS activity could be detected in xylem and leaf epidermal cells, as well as in leaf mesophyll, guard, trichome, and phloem cells. In the stem, activity was detected in phloem, cortical, and parenchyma cells. In the root, GUS activity was present in the root tip and root hair, as well as in most cells in the mature parts of the root.

The possible influence of plant growth conditions upon the different chimeric promoter-uidA constructs had to be accounted for. Hensgens et al., *Plant Mol. Biol.* 20: 921–38 (1992) reported three to ten times higher GUS activity in plant grown in vitro (rooted in sterile agar) compared to plants grown in soil in a greenhouse. Additionally, it has been found that the leaves of plants grown in soil under environmentally controlled conditions express lower levels of GUS activity than do in vitro grown plants. However, the relative levels of GUS activity directed by the various regulatory regions remained approximately the same regardless of how the plants were grown (Table 2, supra). In addition, the relative strengths of the various chimeric regulatory regions in the leaves of F1 progeny of self-pollinated transgenic tobacco plants were similar to those of the original transformed and regenerated plants (Table 2).

A close correlation was found between the steady-state level of mRNA and GUS activity of a particular plant. This result verifies the reliability of using GUS activity assays as a measure of expression strength. This finding is contrary to those of Hensgens et al., supra, however. These opposite findings of Hensgens et al. could be due to their failure to use denaturing conditions for their RNA blot analyses.

Comai et al., supra found that when plants were grown in soil, a mas2' activating sequence and promoter region shorter than that used herein (−301, compared to −318) directed only 10% of the GUS activity as did the CaMV 35S promoter. Inclusion of sequences upstream of −301 elevated the relative GUS activity to 40% that of the 35S promoter. Comai et al. concluded that a region upstream but close to −300 is required for full mas2' promoter activity. The activity of the mas2' promoter (−318), used in experiments described herein, was slightly higher than that directed by the 35S promoter.

Langridge et al., supra showed that the activity of a mas2'-lux fusion gene could be induced several-fold by hormones. Although the initial assays were performed on plants grown in vitro in the presence of hormones, these growth conditions did not greatly affect the results, which is demonstrated by similar relative levels of GUS activity exhibited in plants grown in soil.

Langridge et al. also showed that in stems of transgenic tobacco, mas2' promoter activity was maximally expressed in vascular tissues, whereas Saito et al., supra showed strong staining in the root cap and weaker staining in phloem cells of roots of tobacco. The data disclosed herein correlate well with these previous reports. However, Saito et al. detected GUS activity in the veins, but not in the mesophyll cells of leaves. In the experiments described herein, GUS activity was clearly detected in the mesophyll cells of leaves of transgenic plants harboring a mas2'-uidA chimeric gene. Many of the results described herein also correlate with those of Leung et al. regarding the expression of the mas2' promoter in various tissues of transgenic tobacco plants. Leung et al., however, did not detect GUS activity in stem vascular cells with their constructs.

Combining heterologous ocs or mas activating sequence with a mas or ocs activating sequence plus promoter strongly enhanced the level of GUS activity in all tobacco tissues examined. These data show that the elevated expression of these chimeric regulatory regions results from a cooperative and synergistic interaction, rather than merely additive effects, between the positive regulatory elements found in these chimeric regulatory regions.

EXAMPLE 6
Use of Chimeric Regulatory Regions in Inducible Expression

Another aspect of the invention relates to promoter and upstream activating sequence combinations that are inducible by wounding or pest feeding. One combination developed (AmasPmas) is preferentially expressed in root tissue and induced upon pathogen attack while another (AocsAmasPmas) is more generally expressed, but is further induced by pest attack. These expression systems are useful for genes targeted to root pests, such as nematodes or fungi, and will have applications against insect pests and other leaf pathogens.

Chimeric regulatory regions were constructed using the core mannopine synthase promoter region which had been deleted to −138. This core promoter was fused to GUS coding sequence and terminated by the nopaline synthase ("NOS") poly-adenylation signals. See FIG. 7, construct 1.

Figure 7:
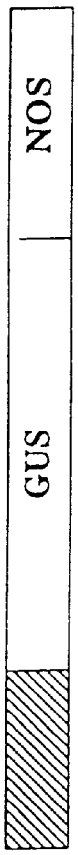
FIG. 7 depicts schematically the constructs used in the inducible expression studies. "UAS"=upstream activating sequence; "pmas"=mas Promoter; "GUS"=β-Glucuronidase Gene; and "NOS"=nopaline synthase poly-adenylation signals.
Figure 7:
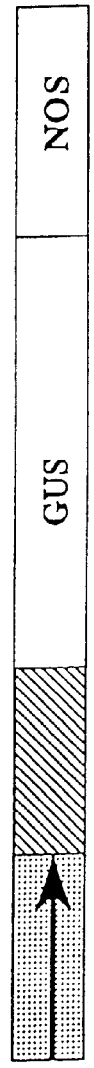
Figure 7:
Figure 7:

The UAS from −318 to −138 of the mannopine synthase promoter was used in conjunction with the mannopine synthase core promoter to create construct 2 of FIG. 7. Constructs 5 and 6 of FIG. 7 contained a trimer of the UAS from the octopine synthase gene from −333 to −116 in both orientations. These constructs were transfected into tobacco using *Agrobacterium tumefaciens* transformation. GUS activity was measured in leaves, stems, and roots of a large number of individual transgenic plants. The activity of the mas promoter and activating sequence (FIG. 7, construct 2) is strongest in the root, and considerably weaker in the leaves and stems. Addition of the ocs activating sequence to the mas activating sequence and promoter (FIG. 7, constructs 5 and 6) increased GUS activity 10 fold in the roots and 50–100 fold in the stems and leaves as compared to construct 2. Orientation of the ocs activating sequence had no effect.

The wound inducibility of the mas promoter plus activating sequence is inducible by 30 fold in leaves, 17 fold in stems, and 3 fold in roots of transgenic tobacco plants.

Figure 8:
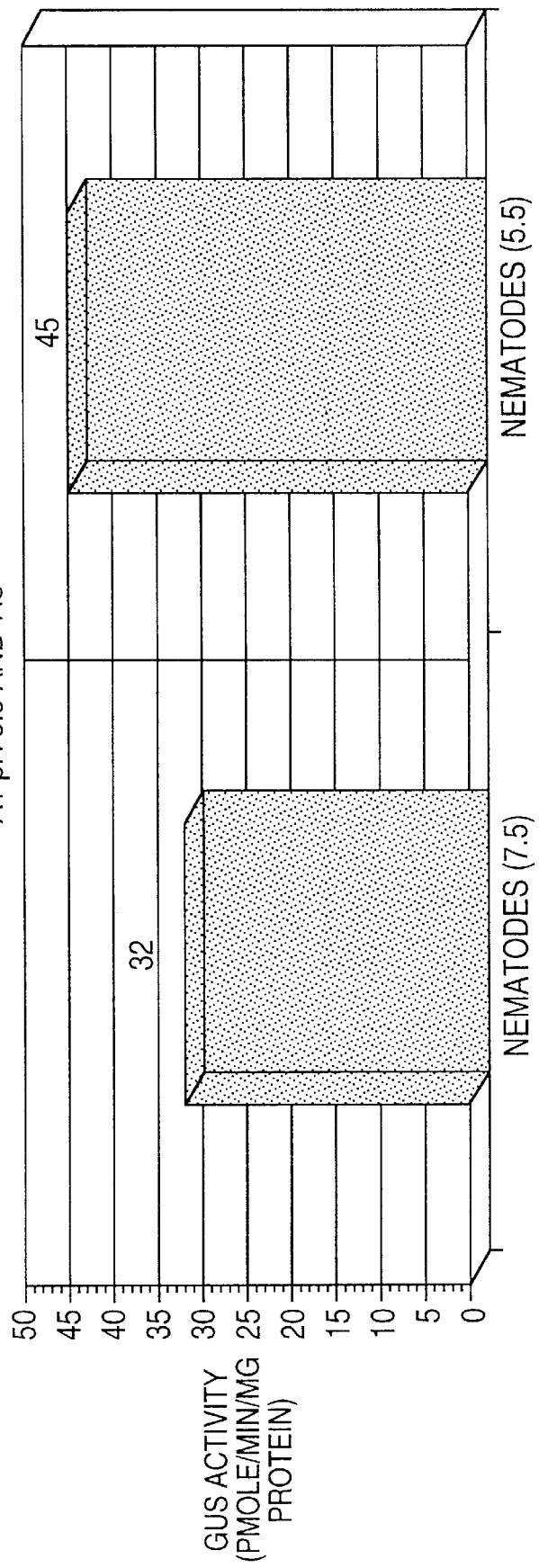
FIG. 8 depicts the level of GUS activity in purified mature nematode eggs. Assays were conducted at pH 5.5 and 7.5 to check for bacterial or animal GUS activities.

To test the inducibility of the various chimeric regulatory regions by pathogen attack, individual transgenic plants containing constructs 1, 2, 5 and 6 were infected with nematodes and monitored for the induction of GUS activity. To ensure that there was no endogenous expression of GUS activity in nematodes, purified preparations of developed nematode eggs were analyzed. The species of nematodes used were *Meloidogyne incognita* race 3 isolated from tomato roots. The mature eggs were isolated by placing infected roots in a 10% chlorox solution for 4 minutes with continuous agitation. The solution was then washed through a 200 mesh screen to remove root debris and the eggs collected on a 500 mesh screen. The eggs were washed and numbers determined using a Nematode Counting Slide (Olympic Equine Products). As a control, to test for the presence of endogenous GUS activity in nematodes, the eggs were then assayed at pH 5.5 and pH 7.5. GUS activity at pH 5.5 is due to endogenous expression originating from animal forms of the gene which would be considered background activity. The GUS activity at pH 7.5 is due to bacterial gene expression. GUS activity in mature nematode eggs was found to be minimal at both pH levels (FIG. 8). *Meloidogyne incognita*, therefore, does not contain either bacterial or animal GUS activities that would cause significant background activity problems in the assay due to presence of nematode eggs.

Transgenic plants were infected with 10,000 purified nematode eggs and grown in sandy soil under greenhouse conditions for several months. Roots from mature plants were harvested and sites of nematode infection visually identified. *Meloidogyne incognita* infection sites can be visually identified by the formation of a root knot which contains the nematode and egg sack while uninfected sites have a normal appearance. Root knots were used to measure GUS activity for infected regions and normal root regions were used as the uninfected control. All comparisons between uninfected and infected roots were based on the same plants and therefore are free from position effects and plant to plant variation in gene expression. Induction of GUS activity was measured in construct 1 using plant number 7 (1-7) at pH 5.5 and 7.5 (FIG. 9, panel A).

Levels of expression were low compared to transgenic plants containing constructs 2, 5, 6 indicating that the Pmas promoter alone only expresses basal levels of activity and is not inducible by nematode infection.

When the Pmas promoter contains the mas activating sequence, Amas (construct 2), expression of GUS activity is high and is inducible by nematode infection (FIG. 9, Panel B). Addition of the UAS of the ocs promoter (Aocs) gave similar induction upon nematode infection (FIG. 9, Panel C). One plant, (5-5) did not show inducible expression. This could be due to the age of the root tissue used or insertion of the gene in a place in the chromosome which caused an alteration in expression since another transformant (5-2) gave the induction response.

These results demonstrate that pathogen infestation induces the chimeric regulatory regions using the mannopine synthase promoter with either the mas or ocs activating sequences. These regions can be used for expressing genes for nematicidal toxins or hormonal compounds that interrupt nematodal feeding and propagation. For example, certain toxins from *Bacillus thuringiensis* ("Bt toxins") have been found that are effective against nematodes. See Adang et al., *Plant Molec. Biol.* 21: 1131–45 (1993). Amino acid sequences for these toxins and nucleotide sequences for genes encoding these toxins are disclosed in U.S. Pat. No. 5,281,530; U.S. Pat. No. 5,322,932; PCT publication WO 92/04453; and European patent publication 0 517 367 A1.

The use of these inducible regulatory regions are not limited to nematicidal applications. These regulatory regions would be equally efficacious against other pathogens that cause a wound.

EXAMPLE 7

Chimeric Regulatory Regions Controlling Expression of Insecticidal Toxins

The chimeric regulatory regions of the present invention can be employed to control the expression of insecticidal toxins in transgenic plants. In a preferred embodiment, Bt toxins can be placed under the control of regulatory regions of the present invention.

Modified genes encoding Bt toxins have been developed to improve levels of expression in transgenic plants. Perlak et al., *Proc. Nat'l Acad. Sci. USA* 88: 3324–28 (1991) discloses modifications to the cryIA gene to replace sequences that are disfavored in plants. These modifications were found to increase the levels of active CryIA toxin. Similarly, Adang et al., supra discloses modifications to the cryIIIA gene for improved expression. Other members of the Bt toxin family would also be amenable to modification, as well as use with the present invention. Genes related to the hypersensitive response may also be employed. See Keen, supra. The present invention is not limited to any specific type of toxin or compound, however. Any type of insecticidal toxin or anti-insect compound that is encoded by genes, or produced by enzymes or other entities encoded by genes, can be used with the present invention.

EXAMPLE 8

Chimeric Regulatory Regions Controlling Expression of Genes for Herbicide Tolerance The chimeric regulatory regions of the present invention can be employed to express in transgenic plants genes that confer tolerance to herbicides. Tolerance to herbicides can be conferred by three primary approaches, namely: (i) plant-mediated detoxification of herbicides; (ii) increased expression of herbicide targets; and (iii) mutation of herbicide binding sites. See Schulz et al., *Crit. Rev. Plant Sci.* 9: 1–15 (1990). Any of the above approaches can be used with the present invention, although the first two approaches are better suited for the present invention.

Several enzymes are known that are capable of detoxifying many of the commonly employed herbicides. For example, glutathione-S-transferases confer tolerance to s-triazine and chloracetamide herbicides. See, for example, Schulz et al., supra; Shah et al., *Plant Molec. Biol.* 6: 203–11 (1986); Weigand et al., *Plant Molec. Biol.* 7: 235–43 (1986). Phosphinothricin has been inactivated by using a gene from *Streptomyces hygroscopicus*. De Block et al., *EMBO J.* 6: 2513–18 (1987); Thompson et al., *EMBO J.* 6: 2519–23 (1987). Nitrilase genes have been found that can detoxify bromoxynil. Stalker et al., *Science* 242: 419–23 (1988). Other detoxifying enzymes can also be used with the present invention.

Another primary tolerance approach is based upon increased expression of the target of a herbicide. For example, glyophosphate is a competitive inhibitor of 5-enolpyruvylshikimate-3-phosphate synthase ("EPSP synthase"). Glyophosphate tolerance can be been imparted by increased expression of EPSP synthase. Increased expression of EPSP synthase can be obtained by using strong, constitutive promoters of the present invention to control expression of EPSP synthase sequences. Additionally, multiple copies of EPSP synthase sequences with promoters according to the present invention can be placed within the transgenic plants in order to obtain still higher levels of expression. Sequences encoding EPSP synthase from various sources are known. See Duncan et al., *FEBS Lett.* 170: 59 (1984); Stalker et al., *J. Biol. Chem.* 260: 4724–28 (1985); Shah et al., *Science* 233: 478–81 (1986).

Finally, altering the site of herbicide binding also can be used to confer herbicide tolerance. Stalker et al. and Shah et al. found that amino acid changes in EPSP synthase could confer resistance to glyophosphate. Similarly, changes in acetohydroxy acid synthase can confer resistance to sulfonylureas and imidazolinones. See Schulz et al., supra; see also Wek et al., *Nucl. Acid. Res.* 13: 3995–4010 (1985).

EXAMPLE 9

Chimeric Regulatory Regions Controlling Expression of Genes for Virus Resistance Virus resistance can be imparted in plants by the expression of viral genes or antisense counterparts of viral genes. The primary approaches for conferring virus resistance is through (i) protein-mediated resistance, usually coat proteins and (ii) antisense RNA-mediated resistance. Beachy et al., *Annu. Rev. Phytopathol.* 28: 451–74 (1990) provides a review of both approaches. Transgenic plants that express a viral coat protein rather than an antisense RNA tend to show greater resistance to viruses. Beachy et al., supra; Cuozzo et al., *Biotechnology* 6: 549–57 (1988).

The regulatory regions of the present invention can be used to express any gene that would confer virus resistance in transgenic plants. For example, the amino acid sequences of many plant virus coat proteins are known, which permits a nucleotide sequence to be deduced. Additionally, the nucleotide sequences of viral coat protein encoding genes are known, which permits synthesis of accurate antisense RNA sequences. These sequences can be expressed in a transgenic plant in order to obtain resistance.

Cuozzo et al., supra discloses sequence coat protein sequences for the cucumber mosaic virus. Transgenic plants containing other viral sequences have been constructed. For example, Anderson et al., *Phytopath.* 79: 1284–90 discloses transgenic plants that express coat proteins of tobacco mosaic virus and alfalfa mosaic virus. Hemenway et al., *EMBO J.* 7: 1273–80 (1988) discloses transgenic plants that express coat protein and antisense RNA for potato virus X. Huisman et al., *J. Gen. Biol.* 69: 1789–98 (1988) discloses sequence for this virus. Gerlach et al., *Nature* 328: 802–05 (1987) disclose transgenic plants that express satellite RNA of the tobacco ringspot virus. This satellite RNA ameliorates the disease symptoms of the ring spot virus. Eggenberger et al., *J. Gen. Virol.* 70: 1853–60 disclose sequence from soybean mosaic virus. The use of the present invention is not limited to any particular type of virus, however. Sequence from any type of virus can be used with the present invention.

It is to be understood that the description, specific examples, figures and data, while indicating preferred embodiments, are given by way of illustration and exemplification and are not intended to limit the present invention. Various changes and modifications within the present invention will become apparent to the skilled artisan from the discussion and disclosure contained herein.

What is claimed is:

1. A cassette for inducible expression of a foreign gene comprising said foreign gene operably linked to a regulatory region comprising a promoter derived from a mannopine synthase gene of *Agrobacterium tumefaciens*, an upstream activating sequence derived from a mannopine synthase gene of *Agrobacterium tumefaciens*, and at least one upstream activating sequence derived from an octopine synthase gene of *Agrobacterium tumefaciens*.

2. A method for nematode inducible expression of a foreign gene in a plant, comprising:
   linking said foreign gene to a regulatory region comprising a promoter derived from a mannopine synthase gene of *Agrobacterium tumefaciens* comprising 138 bases upstream of the transcription initiation site, and an upstream activating sequence derived from a mannopine synthase gene of *Agrobacterium tumefaciens*;
   inserting said foreign gene and said regulatory region in said plant, wherein expression is induced by nematode attack on the plant.

3. A method for nemotode inducible expression of a foreign gene in a plant, comprising:
   linking said foreign gene to a regulatory region comprising a promoter derived from a mannopine synthase gene of *Agrobacterium tumefaciens*, an upstream activating sequence derived from a mannopine synthase gene of *Agrobacterium tumefaciens*, and at least one upstream activating sequence derived from an octopine synthase gene of *Agrobacterium tumefaciens*;
   inserting said foreign gene and said regulatory region in said plant, wherein expression is induced by nematode attack on the plant.

4. A chimeric regulatory region for expressing genes in plants comprising at least three upstream activating sequences derived from an *Agrobacterium tumsfaciens* octopine synthase gene operably linked to a promoter derived from an *Agrobacterium tumefaciens* mannopine synthase gene.

5. A cassette for expressing a foreign gene comprising the foreign gene operably linked to a chimeric regulatory region comprising at least three upstream activating sequences derived from *Agrobacterium tumefaciens* octopine synthase genes operably linked to a promoter derived from an *Agrobacterium tumefaciens* mannopine synthase gene.

6. A plasmid comprising a cassette comprising a foreign gene operably linked to a chimeric regulatory region comprising at least three upstream activating sequences derived from *Agrobacterium tumefaciens* octopine synthase genes operably linked to a promoter derived from an *Agrobacterium tumefaciens* mannopine synthase gene.

7. A method of expressing a foreign gene in a plant, comprising:
   linking said foreign gene to a chimeric regulatory region comprising at least three upstream activating sequences derived from an *Agrobacterium tumefaciens* octopine synthase gene operably linked to a promoter derived from an *Agrobacterium tumefaciens* mannopine synthase gene; and
   inserting said foreign gene and said chimeric regulatory region into a plant, wherein said plant expresses said foreign gene.

8. A transgenic plant comprising a cassette comprising a foreign gene operably linked to a chimeric regulatory region comprising at least three upstream activating sequences derived from *Agrobacterium tumefaciens* octopine synthase genes operably linked to a promoter derived from an *Agrobacterium tumefaciens* mannopine synthase gene.

9. A chimeric regulatory region for expressing genes in plants comprising at least three upstream activating sequences derived from an *Agrobacterium tumefaciens* octopine synthase gene operably linked to an upstream activating sequence derived from an *Agrobacterium tumefaciens* mannopine synthase gene that is operably linked to a promoter derived from an *Agrobacterium tumefaciens* mannopine synthase gene.

10. A cassette for expressing a foreign gene comprising the foreign gene operably linked to a chimeric regulatory region comprising at least three upstream activating sequences derived from *Agrobacterium tumefaciens* octopine synthase genes operably linked to an upstream activating sequence derived from an *Agrobacterium tumefaciens* mannopine synthase gene that is operably linked to a promoter derived from an *Agrobacterium tumefaciens* mannopine synthase gene.

11. A method of expressing a foreign gene in a plant, comprising:

linking said foreign gene to a chimeric regulatory region comprising at least three upstream activating sequences derived from an *Agrobacterium tumefaciens* octopine synthase gene operably linked to an upstream activating sequence derived from an *Agrobacterium tumefaciens* mannopine synthase gene that is operably linked to a promoter derived from an *Agrobacterium tumefaciens* mannopine synthase gene; and inserting said foreign gene and said chimeric regulatory region into a plant, wherein said plant expresses said foreign gene.

12. A transgenic plant comprising a chimeric regulatory region for expressing genes in plants comprising at least three upstream activating sequences derived from an *Agrobacterium tumefaciens* octopine synthase gene operably linked to an upstream activating sequence derived from an *Agrobacterium tumefaciens* mannopine synthase gene that is operably linked to a promoter derived from an *Agrobacterium tumefaciens* mannopine synthase gene.

* * * * *

UNITED STATES PATENT AND TRADEMARK OFFICE
CERTIFICATE OF CORRECTION

PATENT NO. : 5,955,646
DATED : September 21, 1999
INVENTOR(S) : Stanton B. Gelvin et al.

It is certified that error appears in the above-identified patent and that said Letters Patent is hereby corrected as shown below:

Title Page,

Item [75] Inventors: the city for both inventors contains a typographical error wherein "Chandong" should read -- Shandong --.

Item [22] PCT Filed: contains a typographical error wherein the year "1997" should read -- 1994 --.

Column 6,
Line 4, wherein "βglucuronidase" should read -- β-glucuronidase --.

Column 8,
Line 21, wherein "marinopine" should read -- mannopine --.

Column 14,
Line 51, wherein "MRNA" should read -- mRNA --.
Line 60, wherein "nRNA" should read -- mRNA --.

Column 16,
Line 59, wherein "an" should read -- a --.

Signed and Sealed this

Seventh Day of August, 2001

Attest:

NICHOLAS P. GODICI
*Attesting Officer*     *Acting Director of the United States Patent and Trademark Office*